United States Patent
Bartesaghi et al.

(10) Patent No.: US 10,945,989 B2
(45) Date of Patent: Mar. 16, 2021

(54) PERINATAL TREATMENT WITH A FLAVONOID AGONIST OF THE TRKB RECEPTOR FOR BDNF RESCUES NEUROGENESIS AND BEHAVIOR IN THE TS65DN MOUSE MODEL OF DS

(71) Applicant: ALMA MATER STUDIORUM—Universita' di Bologna, Bologna (IT)

(72) Inventors: Renata Bartesaghi, Bologna (IT); Fiorenza Stagni, San Lazzaro di Savena (IT)

(73) Assignee: ALMA MATER STUDIORUM—Universita' di Bologna, Bologna (IT)

( * ) Notice: Subject to any disclaimer, the term of this patent is extended or adjusted under 35 U.S.C. 154(b) by 0 days.

(21) Appl. No.: 16/131,310

(22) Filed: Sep. 14, 2018

(65) Prior Publication Data
US 2019/0083454 A1 Mar. 21, 2019

Related U.S. Application Data

(60) Provisional application No. 62/558,903, filed on Sep. 15, 2017.

(51) Int. Cl.
*A61K 31/352* (2006.01)
*A61P 25/00* (2006.01)

(52) U.S. Cl.
CPC ............ *A61K 31/352* (2013.01); *A61P 25/00* (2018.01)

(58) Field of Classification Search
CPC .. A61K 31/352; C07D 311/32; C07D 311/22; C07D 311/28
See application file for complete search history.

(56) References Cited

PUBLICATIONS

Definition of prevent, Princeton University "About WordNet." WordNet. Princeton University. 2010. <http://wordnet.princeton.edu>, accessed Sep. 18, 2012.*
Bianchi et al. The Journal of Neuroscience 2010, 30 (26), 8769-8779.*
Stagni et al. Experimental Neurology 2017, 298, 79-96.*
Guidi et al. Brain 2014, 137, 380-401.*
Jang S.-W., et al., "A selective TrkB agonist with potent neurotrophic activities by 7,8-dihydroxyflavone," PNAS Feb. 9, 2010, vol. 107, No. 6, pp. 2687-2692.
Liu C., et al., "7,8-dihydroxyflavone, a small molecular TrkB agonist, is useful for treating various BDNF-implicated human disorders," Translational Neurodegeneration (2016) 5:2, pp. 1-9.
Liu X., et al., "A synthetic 7,8-dihydroxyflavone derivative promotes neurogenesis and exhibits potent antidepressant effect," J Med Chem. Dec. 9, 2010; 53(23): 8274-8286.
Tsai T., et al., "7,8-dihydroxyflavone leaeds to survival of cultured embryonic motoneurons by activating intracellular signaling pathways," Molecular and Cellular Neuroscience 56 (2013) 18-28.
Williams R.J., et al., "Flavonoids cognition and dementia: actions, mechanisms, and potential therapeutic utility for Alzheimer disease," Free Radical Biology & Medicine 52 (2012) 35-45.
Zeng Y., et al., "Activation of TrkB by 7,8-dihydroflavone prevents fear memory defects and facilitates amygdalar synaptic plasticity in aging," Journal of Alzheimer's Disease 31 (2012) 765-778.

* cited by examiner

*Primary Examiner* — Irina Neagu
(74) *Attorney, Agent, or Firm* — Silvia Salvadori, P.C.; Silvia Salvadori

(57) ABSTRACT

The present invention relates to methods of restoring brain development in individuals with Down syndrome with a flavone derivative, 7,8-dihydroxyflavone (7,8-DHF).

8 Claims, 13 Drawing Sheets

Figure 1

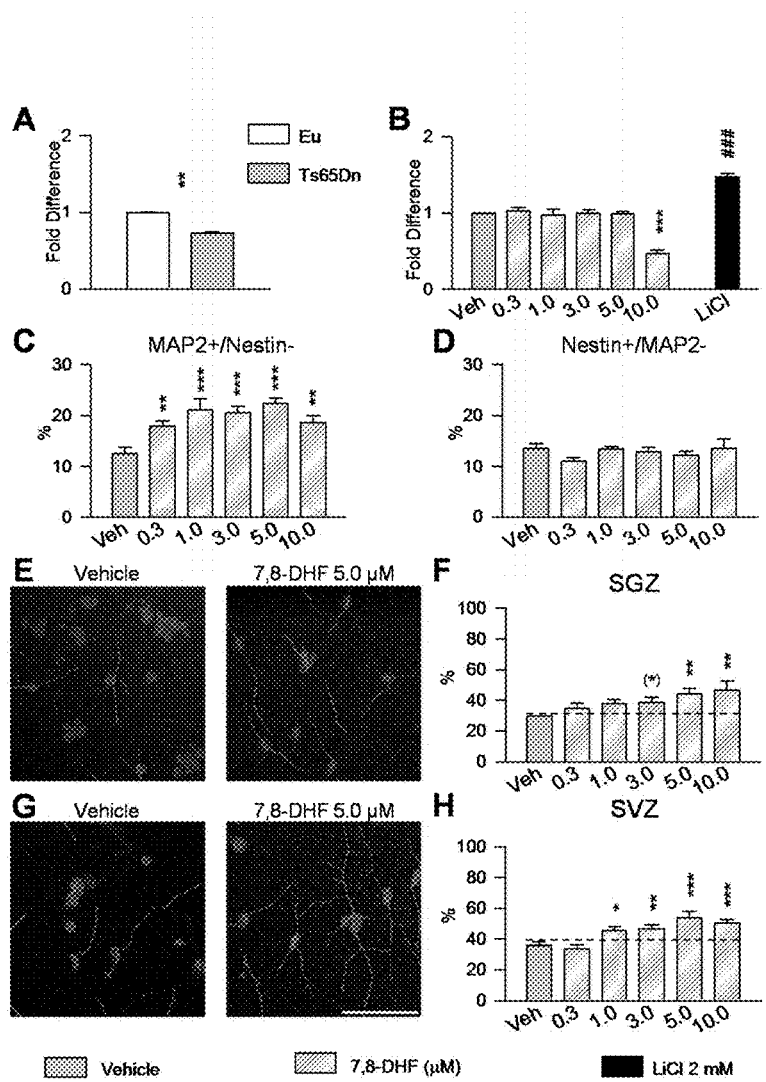

Figure 9:
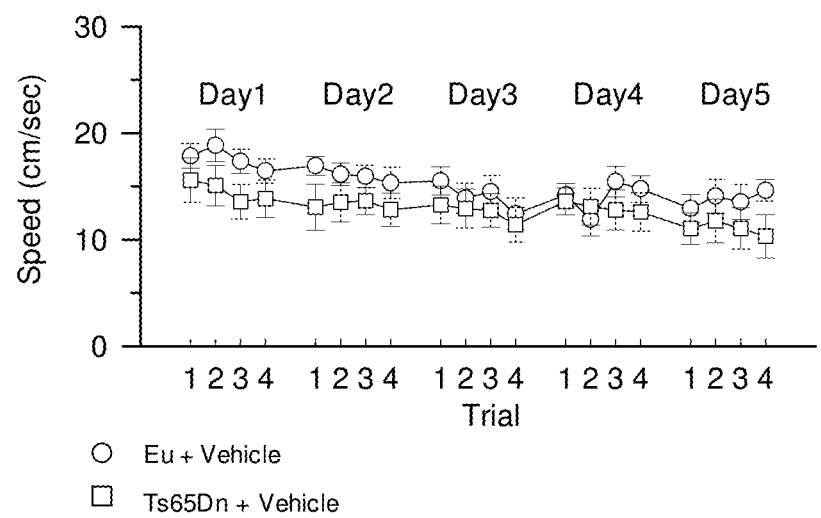

*Fig. 1. Effect of 7,8-DHF on proliferation, differentiation and maturation of trisomic NPCs. A: Number of proliferating cells in cultures of neural progenitor cells (NPCs) from the SVZ of euploid and Ts65Dn mice. Data are expressed as fold change in comparison with euploid NPCs. \*\*p ≤ 0.01, two-tailed t-test. B: Effect of different concentrations of 7,8-DHF or LiCl 2.0 mM on the proliferation rate of NPCs from the SVZ of Ts65Dn mice. Data are expressed as fold change in comparison with NPCs exposed to vehicle alone (DMSO 0.06%). C,D: Percentage of MAP2+/Nestin− cells (C) and of Nestin+/MAP2− cells (D) in cultures of NPCs from the SVZ of Ts65Dn mice grown under differentiating conditions and exposed to different concentrations of 7,8-DHF for 96 h. E–H: Percentage of cells exhibiting neuritic processes (red) in cultures of NPCs from the SGZ (F) and SVZ (H) of Ts65Dn mice grown under differentiating conditions and exposed to different doses of 7,8-DHF for 96 h. Images in (E,G) show cells from the SGZ (E) and SVZ (G) of Ts65Dn mice that were exposed to either vehicle (DMSO 0.02%) or 7,8-DHF 5.0 μM. Scale bar = 50 μm. Data in A–H were obtained in pooled cultures from euploid (n = 4) and Ts65Dn (n = 3) mice. The asterisks in (A, B, C, F, H) indicate a difference in comparison with untreated cultures exposed to DMSO alone [(\*) p ≤ 0.06; \*p ≤ 0.05; \*\*p ≤ 0.01; \*\*\*p ≤ 0.001 (Fisher LSD test after ANOVA)]. The symbol # in (B) indicates a difference between cultures exposed to LiCl and cultures exposed to vehicle alone (### p ≤ 0.001, two-tailed t- test). Abbreviations: 7,8-DHF, 7,8-dihydroxyflavone; Eu, euploid; LiCl, Lithium chloride; MAP2, microtubule associated protein 2; SGZ, subgranular zone; SVZ, subventricular zone.*

Figure 2

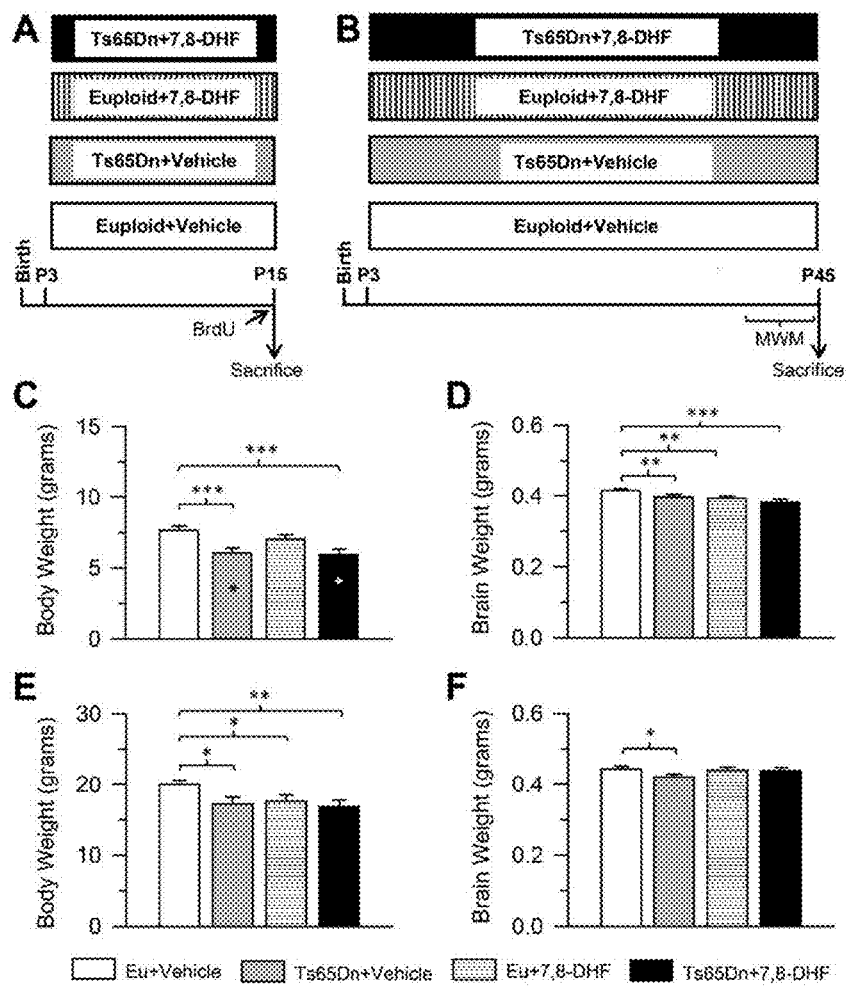

*Fig. 2. Experimental protocol and general results of the in vivo experiments. A: Euploid and Ts65Dn pups received one daily injection of either vehicle or 7,8-DHF from postnatal day 3 (P3) to P15. At P15, mice received one injection of BrdU, and were killed after 2 h in order to evaluate the number of cells in the S-phase of the cell cycle. B: Euploid and Ts65Dn mice received one daily injection of either vehicle or 7,8-DHF from postnatal day P3 to P45-50. These mice were tested with the Morris Water Maze test 6 days before being killed. C,D: Body (C) and brain (D) weight (mean ± SE) in grams of P15 euploid (n = 35) and Ts65Dn (n = 21) mice that received vehicle and euploid (n = 25) and Ts65Dn (n = 15) mice that received 7,8-DHF (5.0 mg/kg) in the period P3-P15. E,F: Body (E) and brain (F) weight (mean ± SE) in grams of P45 euploid (n = 19) and Ts65Dn (n = 14) mice that received vehicle and euploid (n = 17) and Ts65Dn (n = 16) mice that received 7,8-DHF (5.0 mg/kg) in the period P3-P45. \*$p \leq 0.05$; \*\*$p \leq 0.01$; \*\*\*$p \leq 0.001$ (Fisher LSD test after two-way ANOVA). Black asterisks in the gray bar indicate a difference between untreated Ts65Dn mice and treated euploid mice. White asterisks in the black bar indicate a difference between treated Ts65Dn mice and treated euploid mice. Abbreviations: 7,8-DHF, 7,8-dihydroxyflavone; BrdU, 5-bromo-2-deoxyuridine; Eu, euploid; MWM, Morris Water Maze; P, postnatal.*

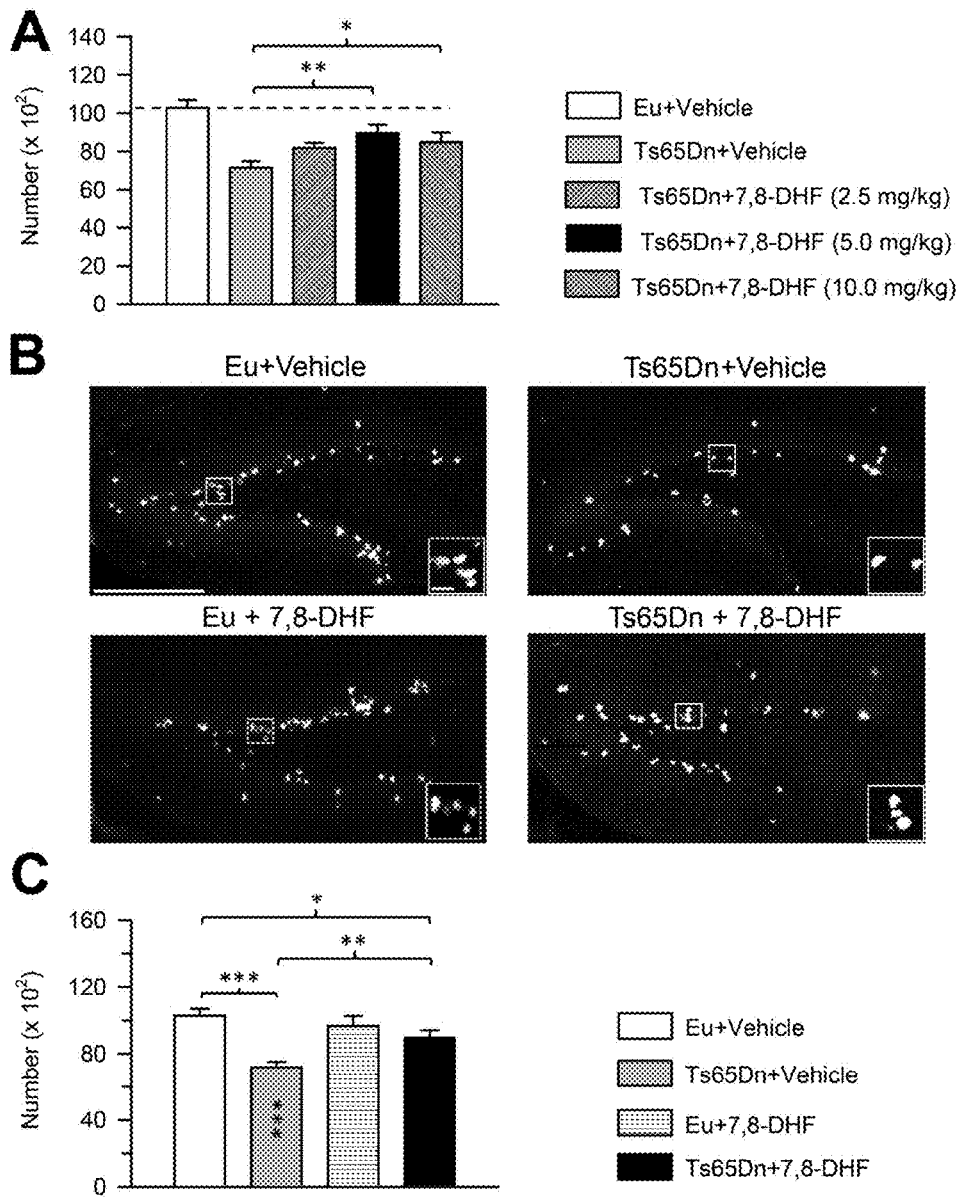

*Fig. 3. Effects of neonatal treatment with 7,8-DHF on the size of the population of cells in the S-phase of the cell cycle in the dentate gyrus (DG) of P15 Ts65Dn and euploid mice. A: In pilot experiments Ts65Dn mice received a daily injection of vehicle (n = 8) or 7,8-DHF (2.5 mg/kg, n = 4; 5.0 mg/kg, n = 5; 10.0 mg/kg, n = 7) in the period P3-P15. At P15, they were injected with BrdU and killed after 2 h. The histograms show the number of BrdU-positive cells in the DG of Ts65Dn mice treated with either vehicle or the indicated doses of 7,8-DHF. The number of BrdU-positive cells in euploid mice reported in (C) that received the vehicle is shown for comparison. B: Representative images of sections immunostained for BrdU from the DG of untreated euploid and Ts65Dn mice and euploid and Ts65Dn mice that were daily treated with 5.0 mg/kg of 7,8-DHF in the period P3-P15. Calibration bar = 200 μm. The insets show zoomed images of the boxed area with examples of individual BrdU-positive cells. Calibration bar = 20 μm. C: Total number of BrdU-positive cells in the DG of untreated euploid (n = 7) and Ts65Dn (n = 8) mice and euploid (n = 3) and Ts65Dn (n = 5) mice treated with 5.0 mg/kg of 7,8-DHF. Values (mean ± SE) in (A) and (C) refer to one hemisphere. \*$p \leq 0.05$; \*\*$p \leq 0.01$; \*\*\*$p \leq 0.001$ (Fisher LSD test after two-way ANOVA). Black asterisks in the gray bar indicate a difference between untreated Ts65Dn mice and treated euploid mice. Abbreviations: 7,8-DHF, 7,8-dihydroxyflavone; Eu, euploid.*

Figure 4

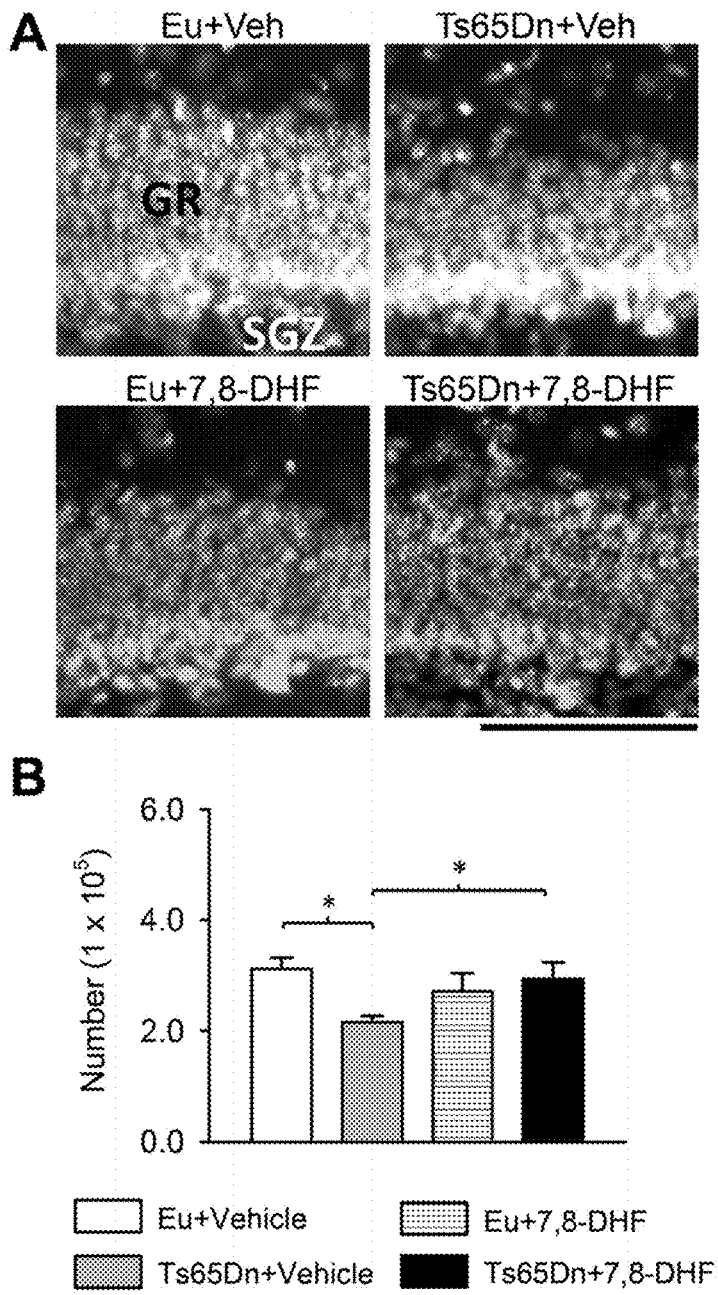

Fig. 4. Effects of neonatal treatment with 7,8-DHF on granule cell number in the dentate gyrus (DG) of P15 Ts65Dn and euploid mice. A: Representative images of Hoechst-stained sections showing the granule cell layer of an animal from each experimental group. Calibration bar = 100 μm. B: Total number of granule cells of untreated euploid (n = 4) and Ts65Dn (n = 4) mice and euploid (n = 4) and Ts65Dn mice (n = 5) treated with 5.0 mg/kg 7,8-DHF. Values (mean ± SE) refer to one DG. *$p \leq 0.05$ (Fisher LSD test after two-way ANOVA). Abbreviations: 7,8-DHF, 7,8-dihydroxyflavone; Eu euploid; GR, granule cell layer; SGZ, subgranular zone; Veh, vehicle.

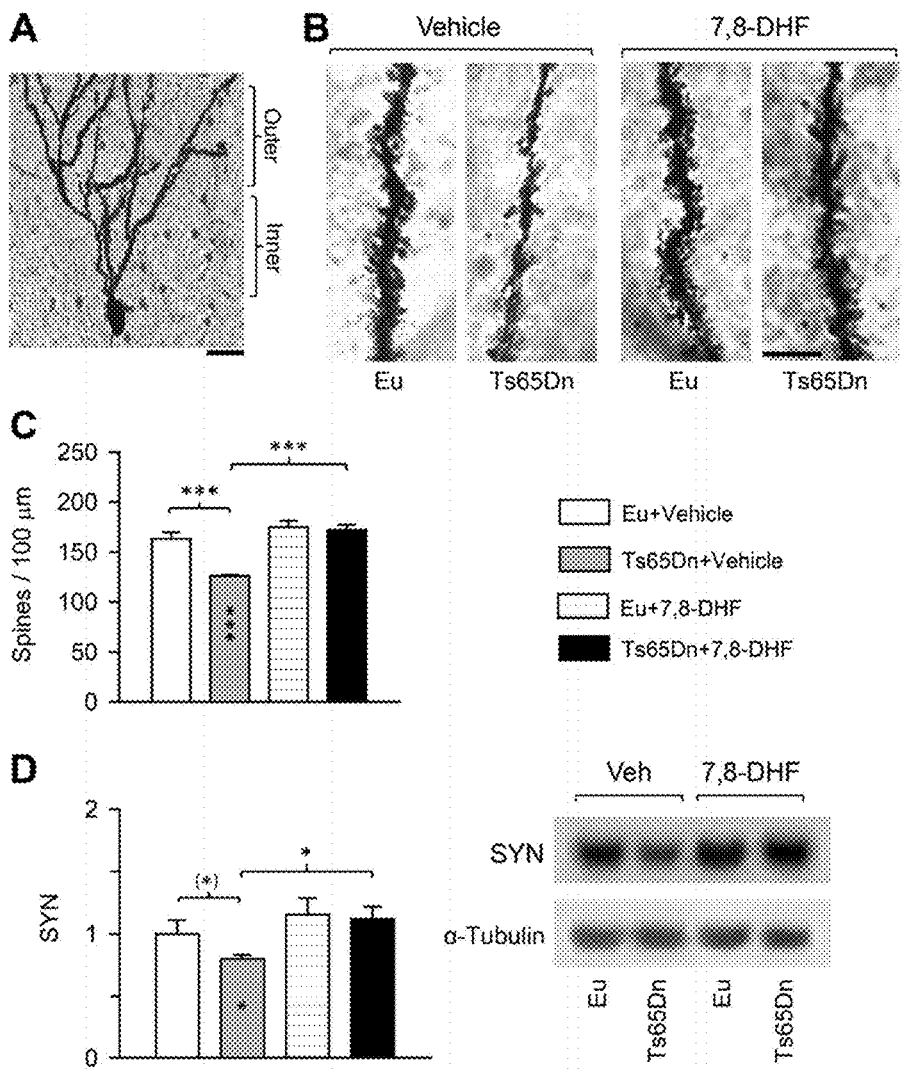

Fig. 5. Effects of neonatal treatment with 7,8- DHF on dendritic spine density and synaptophysin levels in the dentate gyrus of P15 Ts65Dn and euploid mice. A: The photomicrograph shows a Golgi-stained granule cell. Dendritic spines were counted in the inner and outer half of the dendritic arbor of the granule cells. Calibration bar = 10 μm. B: Photomicrograph of Golgi-stained granule cell dendrites showing spines on distal dendritic branches in an animal from each experimental groups. Calibration bar = 5 μm. C: Spine density on the dendritic arbor of the granule cells of untreated euploid (n = 4) and Ts65Dn mice (n = 4) and euploid (n = 4) and Ts65Dn (n = 4) mice treated with 7,8-DHF. D: Western blot analysis of the expression levels of synaptophysin (SYN) in hippocampal homogenates of untreated euploid (n = 10) and Ts65Dn (n = 10) mice and treated euploid (n = 5) and Ts65Dn (n = 6) mice. SYN levels were normalized to GAPDH and expressed as fold difference in comparison with untreated euploid mice. Representative western blots are shown on the right. Values in (C,D) are mean ± SE. (*) $p \leq 0.06$; *$p \leq 0.05$; ***$p \leq 0.001$ (Fisher LSD test after two-way ANOVA). Black asterisks in the gray bar indicate a difference between untreated Ts65Dn mice and treated euploid mice. Abbreviations: 7,8-DHF, 7,8-dihydroxyflavone; Eu, euploid; Veh, Vehicle.

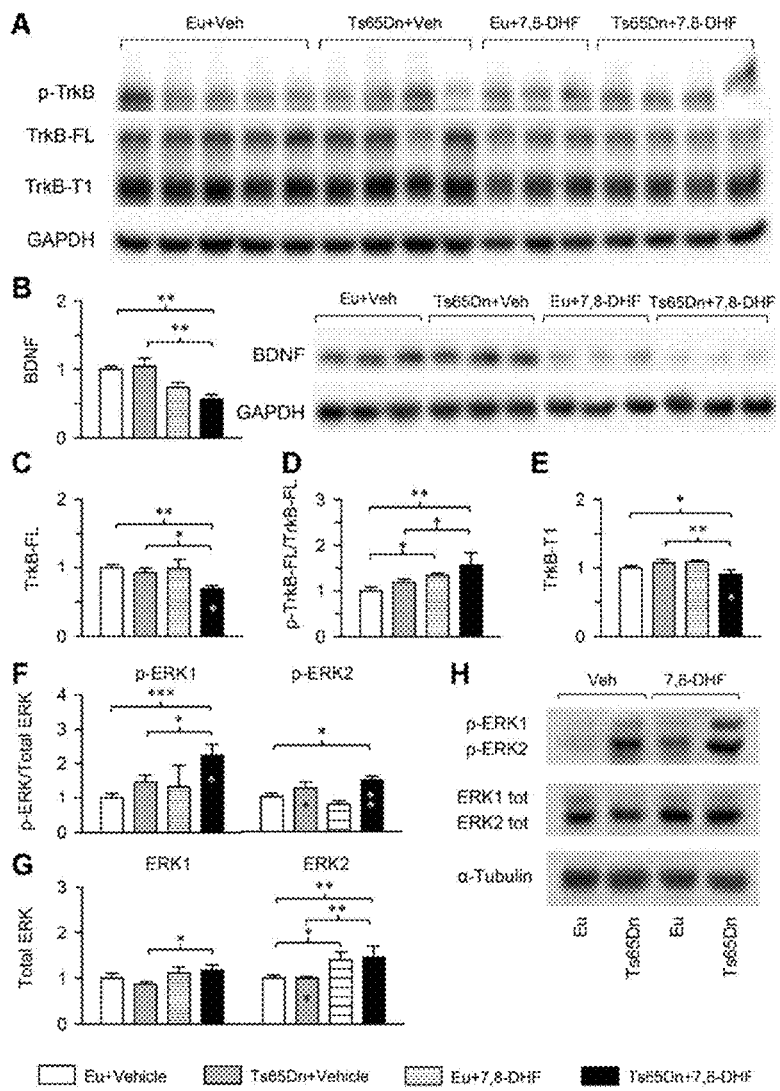

Fig. 6. Effects of neonatal treatment with 7,8-DHF on the BDNF-TrkB receptor system in the hippocampal formation of P15 Ts65Dn and euploid mice. Western blot analysis of the BDNF-TrkB receptor system in the hippocampal formation of P15 Ts65Dn and euploid mice that received either vehicle or 7,8-DHF in the postnatal period P3-P15. A: Representative Western blots showing immunoreactivity for the phosphorylated TrkB receptor (p-TrkB-FL), the full-length TrkB receptor (TrkB-FL), the truncated TrkB receptor (TrkB-T1), and the housekeeping gene GAPDH. B: Levels of BDNF (untreated euploid mice: n = 20; untreated Ts65Dn mice: n = 21; treated euploid mice: n = 5; treated Ts65Dn mice: n = 6) and representative Western blots showing immunoreactivity for BDNF and the housekeeping gene GAPDH. C: Levels of TrkB-FL (untreated euploid mice: n = 19; untreated Ts65Dn mice: n = 19; treated euploid mice: n = 5; treated Ts65Dn mice: n = 6). D: Levels of p- TrkB-FL (untreated euploid mice: n = 15; untreated Ts65Dn mice: n = 16; treated euploid mice: n = 5; treated Ts65Dn mice: n = 6).E: levels of TrkB-T1 (untreated eu- ploid mice: n = 19; untreated Ts65Dn mice: n = 21; treated euploid mice: n = 5; treated Ts65Dn mice: n = 6). F–H: Western blot analysis of p-ERK1/p-ERK2 (untreated euploid mice: n = 10; untreated Ts65Dn mice: n = 12; treated euploid mice: n = 5; treated Ts65Dn mice: n = 6) (F) and total ERK1/ERK2 levels (untreated euploid mice: n = 11; untreated Ts65Dn mice: n = 11; treated euploid mice: n = 5; treated Ts65Dn mice: n = 6) (G) and representative Western blots (H) showing immunoreactivity for p-ERK1, p-ERK2, ERK1, ERK2 and for the housekeeping protein α-Tubulin. Data in (B, C, E) were normalized to GAPDH; data in (G) were normalized to α-Tubulin; data in (D) were normalized to TrkB-FL, and data in (F) were normalized to total ERK1 and total ERK2, respectively. Protein levels (mean ± SE) are expressed as fold difference in comparison with untreated euploid mice. $*p \leq 0.05$; $p \leq 0.01$; $*p \leq 0.001$ (Fisher LSD test after two-way ANOVA). Black asterisks in the gray bar indicate a difference between untreated Ts65Dn mice and treated euploid mice. White asterisks in the black bar indicate a difference between treated Ts65Dn mice and treated euploid mice. Abbreviations: 7,8-DHF, 7,8-dihydroxyflavone; Eu, euploid; Veh, vehicle.

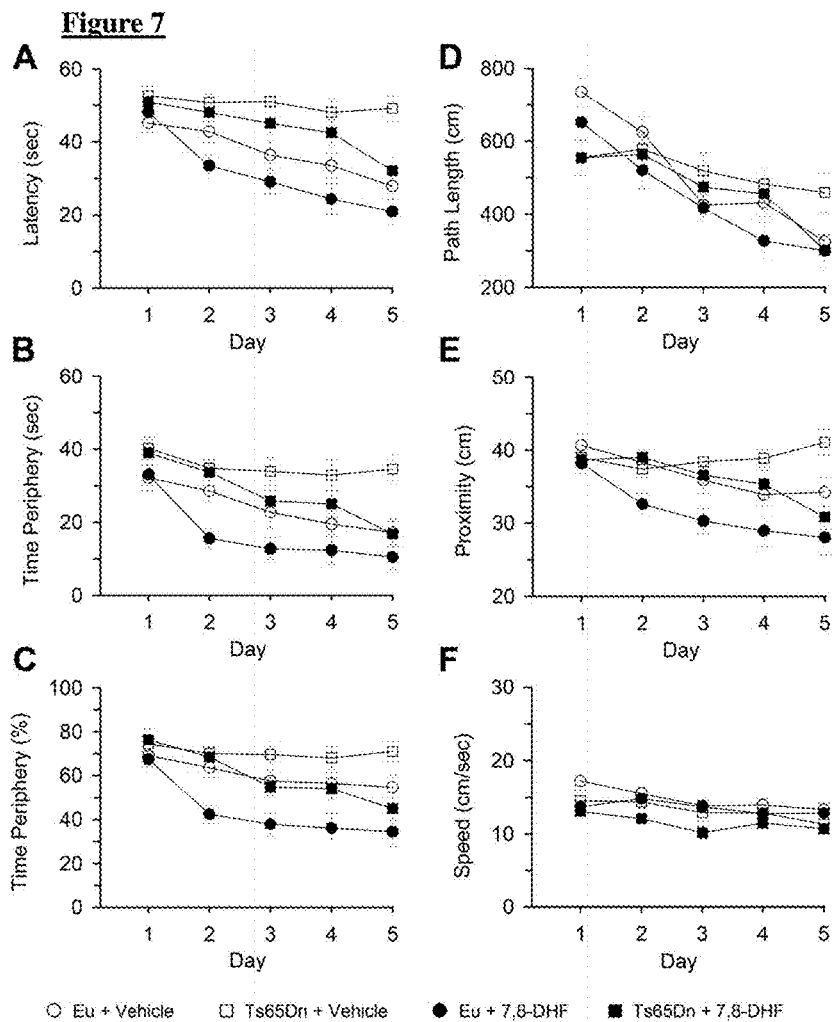

*Fig. 7. Effect of treatment with 7,8-DHF on spatial learning in Ts65Dn and euploid mice. Mice received either vehicle or 7,8-DHF in the period P3-P45-50 and were behaviorally tested with the MWM starting from 6 days before reaching 45–50 days of age (untreated euploid mice: n = 16; untreated Ts65Dn mice: n = 14; treated euploid mice: n = 16; treated Ts65Dn mice: n = 15). The curves in (A–F) report data of euploid mice that received either vehicle (empty circle) or 7,8-DHF (filled circle) and Ts65Dn mice that received either vehicle (empty square) or 7,8-DHF (filled square). A–E: Learning phase of the MWM evaluated as latency to reach the platform (A), time spent at the periphery (thigmotaxis) (B), percentage of time spent at the periphery (C), path length (D), and proximity to the platform zone (E). F: Swimming speed. B–D: Values represent mean ±SE. Abbreviations: 7,8-DHF, 7,8-dihydroxyflavone; Eu, euploid; sec, seconds.*

Figure 8

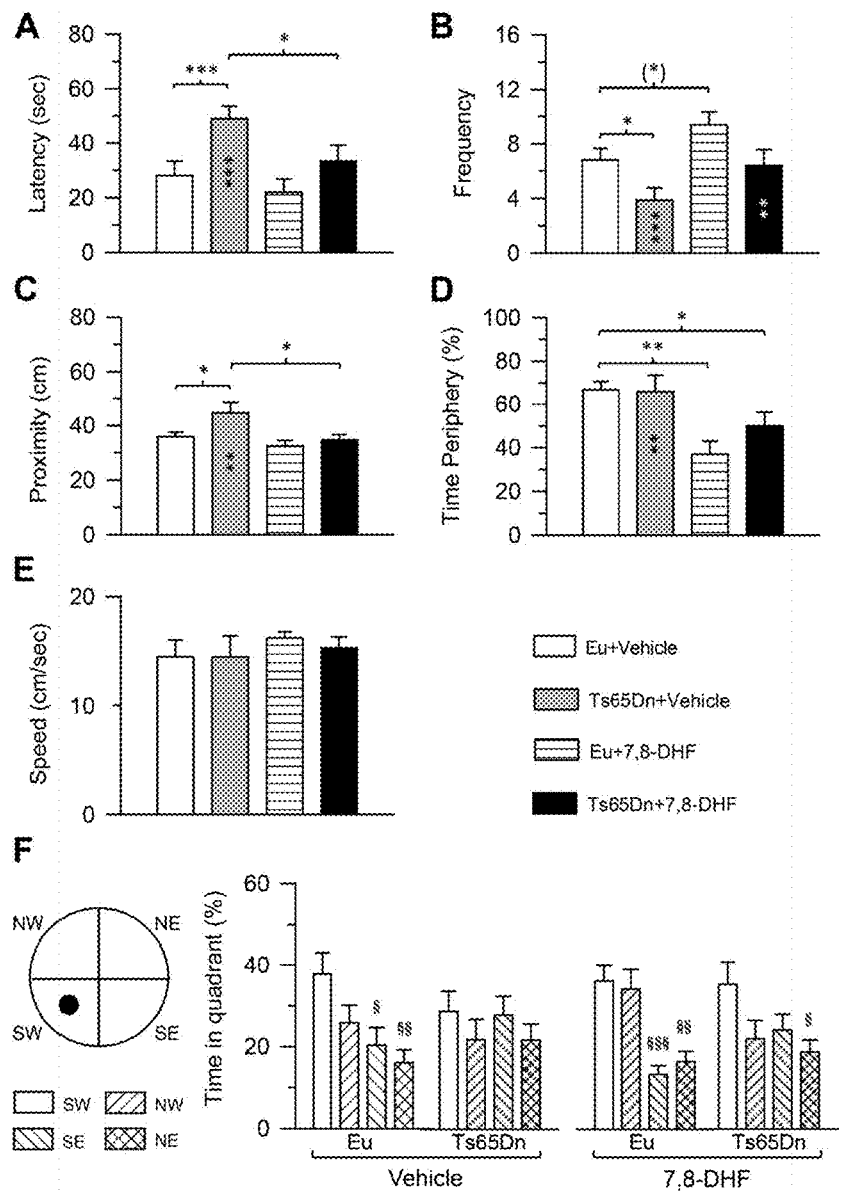

Fig. 8. Effect of treatment with 7,8-DHF on spatial memory in Ts65Dn and euploid mice. Spatial memory was assessed in the probe test after spatial learning (same mice as in Fig. 7). In the probe test, memory was assessed as latency to reach the former platform zone (A), number of crossings (frequency) over the former platform quadrant (B), proximity to the former platform zone (C), percentage of time spent at the periphery (D), percentage of time spent in quadrants (F). E: Swimming speed during the probe test. Values represent mean ± SE. (*) $p \leq 0.06$; *$p \leq 0.05$; $p \leq 0.01$; *$p \leq 0.001$ (Fisher LSD test after ANOVA). Black asterisks in the gray bar indicate a difference between untreated Ts65Dn mice and treated euploid mice; white asterisks in the black bar indicate a difference between treated Ts65Dn mice and treated euploid mice. The symbol§ in (F) indicates a difference between each individual quadrant and the former platform quadrant (see key on the left) for each experimental group. (§) $p \leq 0.06$; § $p \leq 0.05$; §§ $p \leq 0.01$; §§§ $p \leq 0.001$ (two-sample paired t-test). Abbreviations: 7,8-DHF, 7,8-dihydroxyflavone; Eu, euploid; NE, north-east; NW, north-west; SE, south-east; SW, south-west; sec, seconds.

*Fig. 9. Swimming speed of euploid (n=16) and Ts65Dn mice (n=14) in four consecutive trials on each day of the learning phase. Abbreviation: Eu, euploid.*

Figure 10

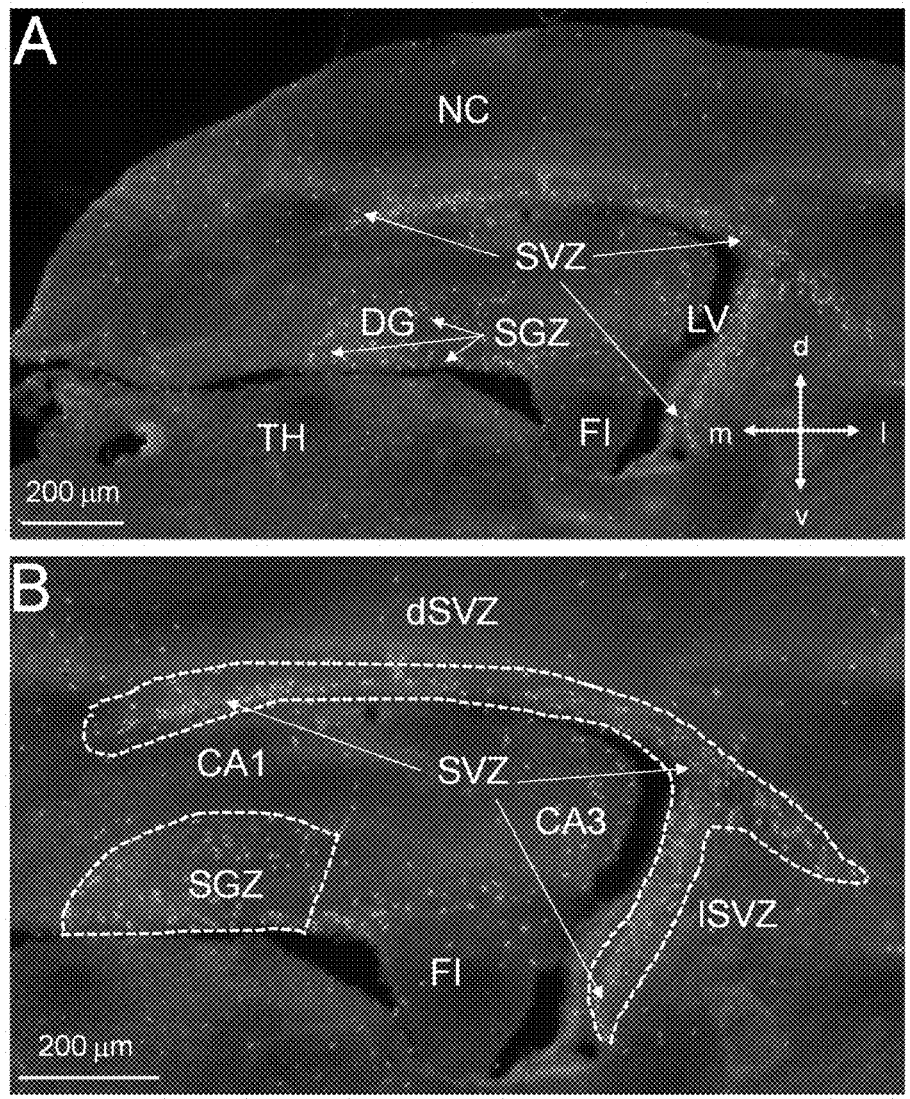

Fig. 10. The neonatal SVZ and SGZ. A: Coronal section across the rostral hippocampal region showing the neonatal SVZ and SGZ. Section was processed for double fluorescence immunohistochemistry for BrdU (red), in order to label cells in the S-phase of the cell cycle, and NeuN (green), a nuclear marker of mature neurons. A large cohort of proliferating cells (red cells) populates the SVZ and the SGZ. Note that scattered proliferating cells are present in the neocortex and thalamus. B: Higher magnification of the same image as in (A) showing the areas of the SVZ and SGZ where cells were counted. Note that at P2, proliferating cells are not segregated in single row below the granule cell layer (the SGZ of the adult brain), but are scattered across the whole perspective layers of the dentate gyrus. All proliferating cells in the dentate gyrus are collectively indicated here as SGZ. The image shows that in the hippocampal formation proliferating cells were also present in the hippocampal fields CA1 and CA3, and in the fimbria. Abbreviations: CA1 and CA3, hippocampal (Cornu Ammonis) fields; d, dorsal; DG, dentate gyrus; dSVZ, dorsal subventricular zone; Eu, euploid; FI, fimbria; l, lateral; lSVZ, lateral subventricular zone; LV, lateral ventricle; m, medial; NC, neocortex; SGZ, subgranular zone; TH, thalamus; v, ventral.

Figure 11

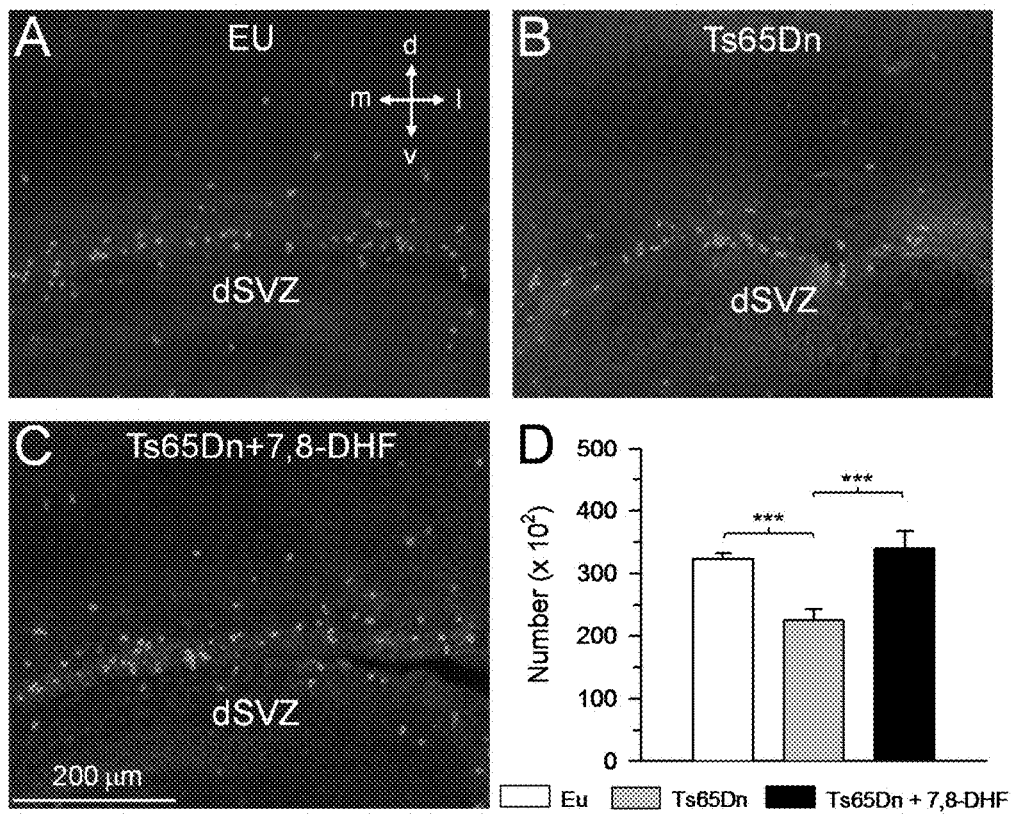

Fig. 11. Effect of prenatal treatment with 7,8-DHF on the number of proliferating cells in the SVZ of Ts65Dn mice. A-C: Coronal sections across the SVZ of an untreated euploid mouse (A), an untreated Ts65Dn mouse (B) and a Ts65Dn mouse treated with 7,8-DHF in the embryonic period E10-E20/21 (C). Sections were processed for double fluorescence immunohistochemistry for BrdU (red), in order to label cells in the S-phase of the cell cycle, and NeuN (green), a nuclear marker of mature neurons. D: Mean number of BrdU-positive cells in the SVZ (dorsal plus lateral part) of untreated euploid mice (n=5), untreated Ts65Dn mice (n=4) and Ts65Dn mice embryonically treated with 7,8-DHF (n=7). Values (mean ±SE) refer to one hemisphere. *** $p < 0.001$ (Fisher LSD test after two-way ANOVA). Abbreviations: 7,8-DHF, 7,8-dihydroxyflavone; d, dorsal; dSVZ, dorsal subventricular zone; Eu, euploid; l, lateral; m, medial; v, ventral.

Figure 12

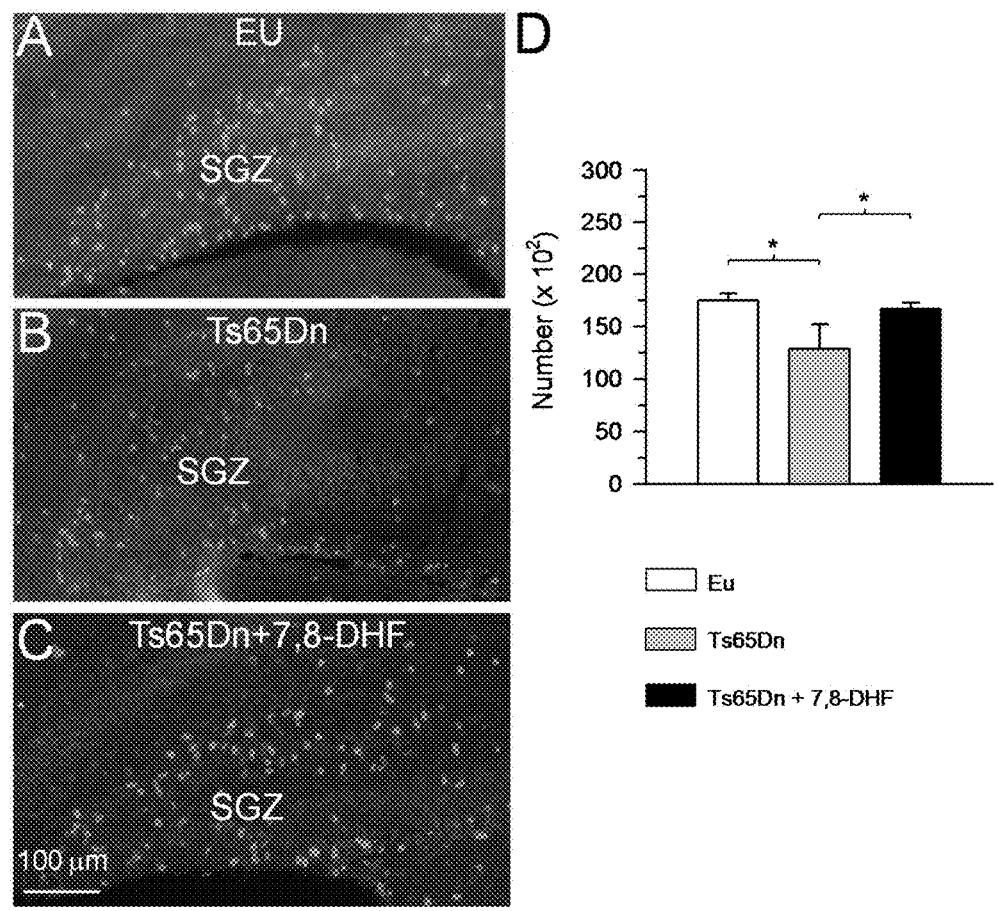

*Fig. 12. Effect of prenatal treatment with 7,8-DHF on the number of proliferating cells in the SGZ of Ts65Dn mice. A-C: Coronal sections across the dentate gyrus of an untreated euploid mouse (A), an untreated Ts65Dn mouse (B) and a Ts65Dn mouse treated with 7,8-DHF in the embryonic period E10-E20/21 (C). Sections were processed for double fluorescence immunohistochemistry for BrdU (red), in order to label cells in the S-phase of the cell cycle, and NeuN (green), a nuclear marker of mature neurons. D: Mean number of BrdU-positive cells in the dentate gyrus of untreated euploid mice (n=5), untreated Ts65Dn mice (n=3) and Ts65Dn mice embryonically treated with 7,8-DHF (n=8). Values (mean ±SE) refer to one hemisphere. * $p < 0.05$ (Fisher LSD test after two-way ANOVA). Abbreviations: 7,8-DHF, 7,8-dihydroxyflavone; d, dorsal; Eu, euploid; l, lateral; m, medial; SGZ, subgranular zone; v, ventral.*

Figure 13:
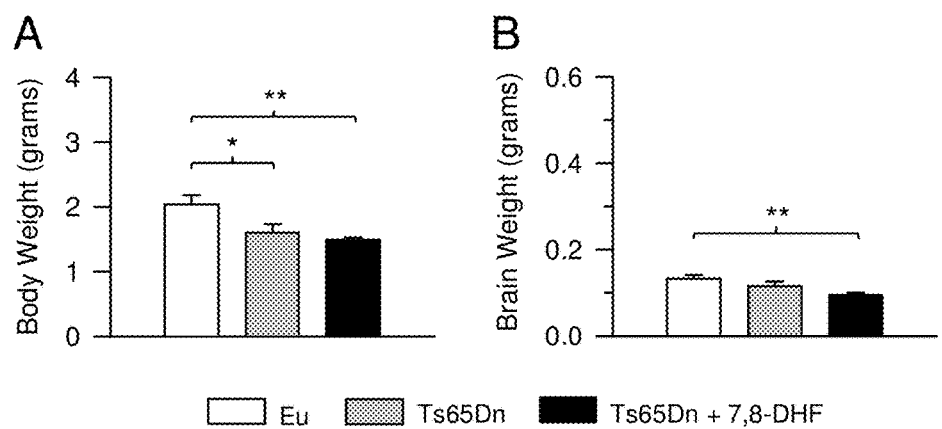

*Fig. 13. Effect of embryonic treatment with 7,8-DHF on body and brain weight. A,B: Body (A) and brain (B) weight in grams of euploid (n=17) and Ts65Dn mice (n=11) that received vehicle and Ts65Dn mice (n=9) that received 7,8-DHF in the embryonic period E10-E20/21, measured on postnatal days 2 (P2). Data are mean ±SE. * p < 0.05; ** p < 0.01 (Fisher LSD test after two-way ANOVA). Abbreviations: 7,8-DHF, 7,8-dihydroxyflavone; Eu, euploid.*

PERINATAL TREATMENT WITH A FLAVONOID AGONIST OF THE TRKB RECEPTOR FOR BDNF RESCUES NEUROGENESIS AND BEHAVIOR IN THE TS65DN MOUSE MODEL OF DS

This non-provisional application claims priority to and the benefit from U.S. Provisional Application Ser. No. 62/558,903 filed on Sep. 15, 2017, the content of which is incorporated herein by reference in its entirety.

The present invention relates to methods of restoring brain development in individuals with Down syndrome.

The article of Stagni et al. "A flavonoid agonist of the TrkB receptor for BDNF improves hippocampal neurogenesis and hippocampus-dependent memory in the Ts65Dn mouse model of DS" (Experimental Neurology, Volume 298, Part A, December 2017, pages 79-96) is inventors' own work (37 C.F.R. § 1.77(b)(6)).

BACKGROUND OF THE INVENTION

Down syndrome (DS) is a relatively common genetic condition (1:750-1000) caused by the triplication of human chromosome 21. One of the most important consequences of trisomy 21 is a delay in neurological development, which manifests progressively as microcephaly and intellectual disability (reviewed by Delabar et al., 2006, Bartesaghi et al., 2011, Dierssen, 2012, Haydar and Reeves, 2012). Neurogenesis reduction and impaired dendritic morphogenesis are the major neurodevelopmental defects of DS and are thought to underlie cognitive disability. The molecular mechanisms underlying brain development alterations are likely to be manifold, due to the complexity of gene imbalance in DS, and no therapies currently exist for the rescue of neurocognitive impairment in DS.

Most of the brain neurons are produced in the prenatal period, with the exception of those involved in the formation of the hippocampus, where neurogenesis continues postnatally and throughout life (Seress et al., 2001; Rice and Barone, 2010; Stiles and Jernigan, 2010; Spalding et al., 2013). Unlike neurogenesis, neuron maturation and the establishment of brain wiring largely take place in the perinatal period.

After the critical periods of neurogenesis and synaptogenesis the brain can undergo relatively limited plastic changes. Thus, the perinatal period represents a window of opportunity for therapies aimed at improving the neurodevelopmental alterations of DS. Since the DS brain starts at a disadvantage, attempts to rescue neurogenesis and neuron maturation should take place as soon as possible.

Previous studies have shown that perinatal treatment with fluoxetine, a selective serotonin reuptake inhibitor (SSRI), fully restores brain development and cognitive performance in the Ts65Dn mouse model of DS (Bianchi et al., 2010b; Guidi et al., 2014). Although fluoxetine is a widely-used antidepressant, that may also be prescribed in children, its use during pregnancy may cause alterations in heart development (Reefhuis et al., 2015). Thus, it is extremely important to find molecules that have the same positive impact as fluoxetine in the trisomic brain but that may pose fewer caveats for clinical application.

The brain-derived neurotrophic factor (BDNF) is a neurotrophin that plays a key role in brain plasticity by specifically binding to tropomyosin-related kinase receptor B (TrkB) (Haniu et al., 1997). This binding causes dimerization and autophosphorylation of the TrkB receptor, which triggers the activity of several intracellular pathways, thereby favoring neurogenesis, neuritogenesis and spine growth (see (Vilar and Mira, 2016)).

Systemic administration of BDNF is impracticable because BDNF has a poor blood-brain barrier penetration. Recent screening of a chemical library has identified a flavone derivative, 7,8-dihydroxyflavone (7,8-DHF), as the first small-molecule compound that penetrates the blood-brain barrier and binds with high affinity and specificity to the TrkB receptor, activates its downstream signaling cascade (Liu et al., 2010 and Liu et al., 2013). Administration of 7,8-DHF enhances the activation of phosphorylated TrkB and increases spine density in several brain regions (Zeng et al., 2012), promotes neurogenesis in the dentate gyrus (Liu et al., 2010), fosters neurite outgrowth (Tsai et al., 2013) and exerts therapeutic efficacy (Liu et al., 2016).

In view of the role of BDNF in fundamental neurodevelopmental processes, Applicants thought that early therapy with the BDNF mimetic 7,8-DHF may restore brain development in individuals with DS.

SUMMARY OF THE INVENTION

The present invention demonstrates that perinatal treatment with 7,8-DHF is able to restore the neurogenesis defects of the DS brain.

In accordance with a first embodiment, the present invention provides for methods of restoring neonatal neurogenesis in the hippocampal formation and other brain regions in subjects in need thereof, said method comprising administering a pharmaceutical composition comprising an effective amount of a TrkB receptor agonist to said subjects and restoring said the hippocampal formation and other brain regions.

A second embodiment of the present invention provides for methods of restoring dendritic spine density in the hippocampal formation and other brain regions in subjects in need thereof, said method comprising administering a pharmaceutical composition comprising an effective amount of a TrkB receptor agonist to said subjects and restoring said dendritic spine density.

A third embodiment of the present invention provides for methods of restoring overall prenatal neurogenesis and intellectual disability in subjects in need thereof, said method comprising administering a pharmaceutical composition comprising an effective amount of a TrkB receptor agonist to said subjects and restoring overall brain development.

An additional embodiment of the invention provides for methods of preventing intellectual disability in subjects affected by Down syndrome said method comprising administering a pharmaceutical composition comprising an effective amount of a TrkB receptor agonist to said subjects and preventing intellectual disability in said subjects.

A further embodiment of the invention provides for methods of treating intellectual disability in subjects affected by Down syndrome said method comprising administering a pharmaceutical composition comprising an effective amount of a TrkB receptor agonist to said subjects and treating said intellectual disability in said subjects.

The TrkB receptor agonist is 7,8-didydroxyflavone and its administration takes places prenatally, perinatally and/or neonataly, orally both to the mothers and to the children, if the administration occurs before birth, or only to the children if the administration occurs after birth.

The administration perinatally includes administration during the period going from approximately the beginning of the second trimester of gestation to the end of the neonatal period.

The administration neonatally includes administration during the period that goes from birth to 10-12 years of age.

The administration prenatally includes administration before birth.

DETAILED DESCRIPTION OF THE INVENTION

To this purpose, we studied the Ts65Dn mouse, a widely-used model of DS. For neonatal treatment, the focus was on the hippocampal formation, one of the most important brain regions involved in pattern separation/completion and memory formation (Rolls, 2016). The hippocampal dentate gyrus mainly develops in the early postnatal period in rodents and continues to produce new neurons throughout life in all species examined including human beings (Altman and Bayer, 1975; Altman and Bayer, 1990a, 1990b; Spalding et al., 2013; Workman et al., 2013). The results show that neonatal treatment with 7,8-DHF restores cellularity and neuron maturation in the hippocampal dentate gyrus of the Ts65Dn model of DS and that these effects are accompanied by restoration of hippocampus-dependent memory. For pre-natal treatment, the subventricular zone (SVZ) and sub-granular zone (SGZ) were examined because they are the two major neurogenic niches of the forebrain. Prenatal treatment with 7,8-DHF fully restores neurogenesis in both the SVZ and SGZ, suggesting that prenatal treatment is a powerful tool to restore overall brain development.

SHORT DESCRIPTION OF THE DRAWINGS

FIG. 1 shows the effect of 7,8-DHF on proliferation, differentiation and maturation of trisomic NPCs. FIG. 1A shows the number of proliferating cells in cultures of neural progenitor cells (NPCs) from the SVZ of euploid and Ts65Dn mice. FIG. 1B shows the effect of different concentrations of 7,8-DHF or LiCl 2.0 mM on the proliferation rate of NPCs from the SVZ of Ts65Dn mice. FIGS. 1C and 1D show percentage of MAP2+/Nestin-cells (1C) and of Nestin+/MAP2+ cells (1D) in cultures of NPCs from the SVZ of Ts65Dn mice grown under differentiating conditions and exposed to different concentrations of 7,8-DHF for 96 h. FIGS. 1E and 1H show percentage of cells exhibiting neuritic processes (red) in cultures of NPCs from the SGZ (1F) and SVZ (1H) of Ts65Dn mice grown under differentiating conditions and exposed to different doses of 7,8-DHF for 96 h. Images in (1E,G) show cells from the SGZ(E) and SVZ (G) of Ts65Dn mice that were exposed to either vehicle (DMSO 0.02%) or 7,8-DHF 5.0 μM.

FIG. 2 shows the experimental protocol and general results of the in vivo experiments. FIG. 2A shows euploid and Ts65Dn pups which received one daily injection of either vehicle or 7,8-DHF from postnatal day 3 (P3) to P15. FIG. 2B shows euploid and Ts65Dn mice which received one daily injection of either vehicle or 7,8-DHF from postnatal day P3 to P45-50. FIGS. 2C e 2D: Body (2C) and brain (2D) weight (mean±SE) in grams of P15 euploid (n=35) and Ts65Dn (n=21) mice that received vehicle and euploid (n=25) and Ts65Dn (n=15) mice that received 7,8-DHF (5.0 mg/kg) in the period P3-P15. FIGS. 2E and 2F: Body (2E) and brain (2F) weight (mean±SE) in grams of P45 euploid (n=19) and Ts65Dn (n=14) mice that received vehicle and euploid (n=17) and Ts65Dn (n=16) mice that received 7,8-DHF (5.0 mg/kg) in the period P3-P45.

FIG. 3 shows the effects of neonatal treatment with 7,8-DHF on the size of the population of cells in the S-phase of the cell cycle in the dentate gyrus (DG) of P15 Ts65Dn and euploid mice. FIG. 3A shows Ts65Dn mice which received a daily injection of vehicle (n=8) or 7,8-DHF (2.5 mg/kg, n=4; 5.0 mg/kg, n=5; 10.0 mg/kg, n=7) in the period P3-P15. FIG. 3B shows representative images of sections immunostained for BrdU from the DG of untreated euploid and Ts65Dn mice and euploid and Ts65Dn mice that were daily treated with 5.0 mg/kg of 7,8-DHF in the period P3-P15. FIG. 3C shows the total number of BrdU-positive cells in the DG of untreated euploid (n=7) and Ts65Dn (n=8) mice and euploid (n=3) and Ts65Dn (n=5) mice treated with 5.0 mg/kg of 7,8-DHF.

FIG. 4 shows the effects of neonatal treatment with 7,8-DHF on granule cell number in the dentate gyrus (DG) of P15 Ts65Dn and euploid mice. FIG. 4A shows representative images of Hoechst-stained sections showing the granule cell layer of an animal from each experimental group. FIG. 4B shows the total number of granule cells of untreated euploid (n=4) and Ts65Dn (n=4) mice and euploid (n=4) and Ts65Dn mice (n=5) treated with 5.0 mg/kg 7,8-DHF.

FIG. 5 shows the effects of neonatal treatment with 7,8-DHF on dendritic spine density and synaptophysin levels in the dentate gyrus of P15 Ts65Dn and euploid mice. FIG. 5A shows a Golgi-stained granule cell. FIG. 5B is a photomicrograph of Golgi-stained granule cell dendrites showing spines on distal dendritic branches in an animal from each experimental groups. FIG. 5C shows the spine density on the dendritic arbor of the granule cells of untreated euploid (n=4) and Ts65Dn mice (n=4) and euploid (n=4) and Ts65Dn (n=4) mice treated with 7,8-DHF. FIG. 5D shows a Western blot analysis of the expression levels of synaptophysin (SYN) in hippocampal homogenates of untreated euploid (n=10) and Ts65Dn (n=10) mice and treated euploid (n=5) and Ts65Dn (n=6) mice.

FIG. 6 shows the effects of neonatal treatment with 7,8-DHF on the BDNF-TrkB receptor system in the hippocampal formation of P15 Ts65Dn and euploid mice. FIG. 6A are representative Western blots showing immunoreactivity for the phosphorylated TrkB receptor (p-TrkB-FL), the full-length TrkB receptor (TrkB-FL), the truncated TrkB receptor (TrkB-T1), and the housekeeping gene GAPDH. FIG. 6B shows levels of BDNF (untreated euploid mice: n=20; untreated Ts65Dn mice: n=21; treated euploid mice: n=5; treated Ts65Dn mice: n=6) and representative Western blots showing immunoreactivity for BDNF and the housekeeping gene GAPDH. FIG. 6C shows levels of TrkB-FL (untreated euploid mice: n=19; untreated Ts65Dn mice: n=19; treated euploid mice: n=5; treated Ts65Dn mice: n=6). FIG. 6D shows levels of p-TrkB-FL (untreated euploid mice: n=15; untreated Ts65Dn mice: n=16; treated euploid mice: n=5; treated Ts65Dn mice: n=6). FIG. 6E shows levels of TrkB-T1 (untreated euploid mice: n=19; untreated Ts65Dn mice: n=21; treated euploid mice: n=5; treated Ts65Dn mice: n=6). FIGS. 6F-6H show Western blot analysis of p-ERK1/p-ERK2 (untreated euploid mice: n=10; untreated Ts65Dn mice: n=12; treated euploid mice: n=5; treated Ts65Dn mice: n=6) (6F) and total ERK1/ERK2 levels (untreated euploid mice: n=11; untreated Ts65Dn mice: n=11; treated euploid mice: n=5; treated Ts65Dn mice: n=6) (6G) and representative Western blots (6H) showing immunoreactivity for p-ERK1, p-ERK2, ERK1, ERK2 and for the housekeeping protein α-Tubulin.

FIG. 7 shows the effect of treatment with 7,8-DHF on spatial learning in Ts65Dn and euploid mice. The curves in FIGS. 7A-7F report data of euploid mice that received either vehicle (empty circle) or 7,8-DHF (filled circle) and Ts65Dn mice that received either vehicle (empty square) or 7,8-DHF (filled square). FIGS. 7A-7E show the learning phase of the MWM evaluated as latency to reach the platform (7A), time spent at the periphery (thigmotaxis) (7B), percentage of time spent at the periphery (7C), path length (7D), and proximity to the platform zone (7E). FIG. 7F shows swimming speed.

FIG. 8 shows the effect of treatment with 7,8-DHF on spatial memory in Ts65Dn and euploid mice. Spatial memory was assessed in the probe test after spatial learning (same mice as in FIG. 7). In the probe test, memory was assessed as latency to reach the former platform zone (8A), number of crossings (frequency) over the former platform quadrant (8B), proximity to the former platform zone (8C), percentage of time spent at the periphery (8D), percentage of time spent in quadrants (8F). FIG. 8E shows the swimming speed during the probe test.

FIG. 9 shows the speed of euploid (n=16) and Ts65Dn mice (n=14) in four consecutive trials on each day of the learning phase.

FIG. 10 shows the neonatal SVZ and SGZ. FIG. 10A shows a coronal section across the rostral hippocampal region showing the neonatal SVZ and SGZ. FIG. 10B shows a higher magnification of the same image as in (10A) showing the areas of the SVZ and SGZ where cells were counted.

FIG. 11 shows the effect of prenatal treatment with 7,8-DHF on the number of proliferating cells in the SVZ of Ts65Dn mice. FIG. 11A shows proliferating cells in the SVZ of an untreated euploid mouse. FIG. 11B shows proliferating cells in the SVZ of an untreated Ts65Dn mouse and FIG. 11C shows proliferating cells in the SVZ of a Ts65Dn mouse treated with 7,8-DHF in the embryonic period E10-E20/21. FIG. 11D shows the mean number of proliferating cells in the SVZ of untreated euploid and Ts65Dn mice and Ts65Dn mice treated with 7,8-DHF in the embryonic period E10-E20/21.

FIG. 12 shows the effect of prenatal treatment with 7,8-DHF on the number of proliferating cells in the SGZ of Ts65Dn mice. FIG. 12A shows proliferating cells in the SGZ of an untreated euploid mouse. FIG. 12B shows proliferating cells in the SGZ of an untreated Ts65Dn mouse and FIG. 12C shows proliferating cells in the SGZ of a Ts65Dn mouse treated with 7,8-DHF in the embryonic period E10-E20/21. FIG. 12D shows the mean number of proliferating cells in the SGZ of untreated euploid and Ts65Dn mice and Ts65Dn mice treated with 7,8-DHF in the embryonic period E10-E20/21.

FIG. 13 shows the effect of embryonic treatment with 7,8-DHF on body and brain weight of euploid and Ts65Dn mice. FIG. 13A shows the effect of treatment on the body weight and FIG. 13B shows the effect of treatment on the brain weight.

EXAMPLES

Effect of Neonatal Treatment with 7,8-DHF: Neonatal Treatment with 7,8-DHF Restores Hippocampal Neurogenesis, Spinogenesis and Hippocampus-Dependent Memory 1. Colony Ts65Dn mice were generated by mating B6EiC3Sn a/A-Ts(17^16) 65Dn females with C57BL/6JEiJ×C3H/HeSnJ (B6EiC3Sn) F1 hybrid males. This parental generation was provided by Jackson Laboratories (Bar Harbor, Me., USA). To maintain the original genetic background, the mice used were of the first generation of this breeding. Animals were genotyped as previously described (Reinholdt et al., 2011). Because C3H/HeSnJ mice carry a recessive mutation that leads to retinal degeneration, animals used for the behavioral study were genotyped by standard PCR to screen out all mice carrying this gene. The day of birth was designated postnatal day zero (P0). The animals' health and comfort were controlled by the veterinary service. The animals had access to water and food ad libitum and lived in a room with a 12:12 h light/dark cycle. Experiments were performed in accordance with the European Communities Council Directive of 24 Nov. 1986 (86/609/EEC) for the use of experimental animals and were approved by Italian Ministry of Public Health (813/2016-PR). In this study, all efforts were made to minimize animal suffering and to keep the number of animals used to a minimum.

2. In Vitro Experiments

Cultures of SVZ or SGZ Neural Progenitor Cells

Cells were isolated from the subventricular zone (SVZ) of the lateral ventricle and the subgranular zone (SGZ) of the hippocampal dentate gyrus (DG) of newborn (P1-P2) euploid and Ts65Dn mice. Briefly, brains were removed, the SVZ and SGZ regions were isolated and individually collected in ice-cold PIPES buffer pH 7.4. After centrifugation, tissue was digested for 10 min at 37° C. using Trypsin/EDTA 0.25% (Life Technologies) aided by gentle mechanical dissociation. Cell suspension from each individual mouse was plated onto 25 cm$^2$ cell-culture flask (Thermo Fisher Scientific) and cultured as floating neurospheres in medium containing basic fibroblast growth factor (bFGF, 10 ng/ml; Peprotech) and epidermal growth factor (EGF, 20 ng/ml; Peprotech) using an established protocol (Meneghini et al., 2014). Primary (Passage 1, P1) neurospheres were dissociated using Stem-proAccutase (Life Technologies) after 7 days in vitro (DIV), thereafter neurospheres were passaged every 5 DIV. For proliferation studies neurospheres (P3-P12) from the SVZ were dissociated in a single cell suspension and plated onto Nunclon™ Delta Surface 96-wellplate (Thermo Fisher Scientific) at a density of 4×10$^3$ cells per well in DMEM/F-12 medium supplemented with B27, Glutamax™, heparinsodium salt (4 µg/ml; ACROS Organics), bFGF (10 ng/ml) and 100 U/100 µg/ml Penicillin/Streptomycin (Life Technologies) in presence of 7,8-Dihydroxyflavone (7,8-DHF; 0.3-10.0 µM, Sigma Aldrich) or its vehicle (DMSO0.06%) for 96 h. Since lithium has been shown to restore proliferation of NPCs of Ts65Dn mice in vivo (Bianchi et al., 2010a; Contestabile et al., 2013) and in vitro (Trazzi et al., 2014), the effect of exposure to lithium 2 mM was also examined, as positive control. This dose was chosen based on previous evidence (Trazzi et al., 2014). Cell proliferation was quantified as relative luminescence units (RLU) values using Cell Titer-Glo viability assay reagent (Promega) on aVictor$^3$-V plate reader (PerkinElmer). For differentiation experiments neurospheres from the SVZ and SGZ were dissociated into single cells and plated onto laminin-coated Lab-Tek 8-well permanoxchamberslides (ThermoFisher Scientific) at a density of 35×10$^3$ per well in differentiation medium (DMEM-F12 supplemented with B27, 2 mM Glutamax and 100 U/100 mg/ml penicillin/streptomycin). NPCs were treated in presence of 7,8-DHF (0.3-10.0 µM, Sigma Aldrich) or vehicle (DMSO 0.02%) for 96 h. Phenotypic characterization of NPC-derived cells was carried out by immunolocalization for MAP2 (rabbitpolyclonal, 1:600; Millipore) and Nestin (chicken monoclonal, 1:1500; Neuromics). Secondary antibodies were as follows: AlexaFluor555-conjugated goat anti rabbit (1:1400; Molecular Probes); AlexaFluor488-conjugated goat anti chicken (1:1400; Molecular Probes). Nuclei were counterstained with 0.8 ng/ml Hoechst (Thermo Fisher Scientific) diluted in PBS. In each experiment, five fields/well (corresponding to about 150-200 cells/well) were counted with a 60× objective by a Leica DMIRB inverted fluorescence microscope. Immunoreactive cells were counted and their percentage over total viable cells was calculated. The number of MAP2 cells exhibiting neuritic processes was counted at random locations in five fields/well and their number was expressed as percentage over total cell number in each sampled location. All experiments were run in triplicate.

3. In Vivo Experiments

Treatment with either 7,8-DHF or vehicle began on postnatal day 3(P3). All mice that survived in the P0 to P3 period entered this study, with no specific selection criteria. Total of 185 mice entered the study (96 males and 89 females). The number of vehicle-treated and 7,8-DHF treated mice was 96 and 89, respectively. Seven vehicle-treated (7.3%) and five 7,8-DHF-treated (5.6%) mice died before weaning, in the P6-P22 period. The similarity in the mortality rate across groups suggests that treatment has no adverse effects on the health of mice.

3.1 Experimental Protocol of In Vivo Experiments

Pilot Experiment

In a pilot study we tested the effects of different doses of 7,8-DHF on the proliferation rate in the SGZ of Ts65Dn mice. Mice received a daily subcutaneous injection of 7,8-DHF (2.5, 5.0, or 10.0 mg/kg in PBS with 1-2% DMSO) from postnatal day 3 (P3) to P15. On P15, mice received an intraperitoneal injection (150 µg/g body weight) of BrdU (5-bromo-2-deoxyuridine; Sigma), a marker of cells in the S-phase of the cell cycle (Nowakowski et al., 1989) in TrisHCl 50 mM 2 h before being killed and the number of BrdU positive cells in the SGZ was evaluated. We found that the optimum dose was 5.0 mg/kg (see FIG. 3A). Therefore, this study (Experiment 1 and Experiment 2) was carried out using a 5.0 mg/kg dose.

a)

Euploid and Ts65Dn mice received a daily subcutaneous injection (at 9-10 am) of 7,8-DHF (5.0 mg/kg in vehicle: PBS with 1% DMSO) or vehicle from postnatal day 3 (P3) to postnatal day 15. This timing was chosen because it corresponds to that previously used to test the effects of fluoxetine and other pharmacotherapies in the neonate Ts65Dn mouse (Bianchi et al., 2010b; Giacomini et al., 2015; Stagni et al., 2016). Mice that received 7,8-DHF will be called "treated mice" (treated euploid mice: n=25; treated Ts65Dn mice: n=15). Mice that received the vehicle will be called "untreated mice" (untreated euploid mice: n=35; untreated Ts65Dn mice: n=21). On P15, mice received an intraperitoneal injection (150 µg/g body weight) of BrdU in TrisHCl 50 mM 2 h before being killed (FIG. 2A). The brains were excised and cut along the midline. The left hemisphere of a group of mice was fixed by immersion in PFA 4% and frozen, and the left hemisphere of another group of mice was used for Golgi staining. The right hemispheres of all mice was kept at −80° C. and used for western blotting.

b)

Euploid and Ts65Dn mice received a daily subcutaneous injection (at 9-10 am) of 7,8-DHF (5.0 mg/kg in vehicle) or vehicle from postnatal day 3 (P3) to postnatal day P45-P50. Mice that did not carry a recessive mutation that leads to retinal degeneration entered the behavioral study (untreated euploid mice: n=19; untreated Ts65Dn mice: n=14; treated euploid mice: n=17; treated Ts65Dn mice: n=16). These mice will be called here P45 mice. Mice were behaviorally tested in the 6 days that preceded the day of sacrifice (FIG. 2B).

The body weight of mice of all groups was recorded prior to sacrifice and the brain weight was recorded immediately after brain removal. The number of animals used for each experimental procedure is specified in the figure legends and in Table 3.

3.2 Histological Procedures

The frozen brains were cut with a freezing microtome into 30-µm-thick coronal sections that were serially collected in anti-freezing solution (30% glycerol; 30% ethylene glycol; 10% PBS10×; sodium azide 0.02%; MilliQ to volume).

3.3 Immunohistochemistry

Immunohistochemistry (IHC) was carried out as previously described (Contestabile et al., 2007; Bianchi et al., 2010b; Guidi et al., 2013; Giacomini et al., 2015).

BrdU immunohistochemistry

One out of six free-floating sections (n=15-18 sections) from the hippocampal formation of P15 mice was incubated with rat anti-BrdU antibody. Detection was performed with a Cy3-conjugated anti rat-secondary antibody as indicated in Table 1.

3.4 Golgi Staining

Brains of P15 mice were Golgi stained using the FD Rapid Golgi Stain™ Kit (FD NeuroTechnologies, Inc.). Brains were immersed in the impregnation solution containing mercuric chloride, potassium dichromate and potassium chromate and stored at room temperature in darkness for 3 weeks. Hemispheres were cut with a microtome in 90-µm-thick coronal sections that were mounted on gelatin-coated slides and were air dried at room temperature in the dark for one day. After drying, sections were rinsed with distilled water and subsequently stained in a developing solution (FD Rapid Golgi Stain Kit).

3.5 Measurements

Image Acquisition Immunofluorescence images were taken with a Nikon Eclipse TE 2000-S inverted microscope (Nikon Corp., Kawasaki, Japan), equipped with a Nikon digital camera DS 2MBWc. Measurements were carried out using the software Image Pro Plus (Media Cybernetics, Silver Spring, Md. 20910, USA). Bright field images were taken on a light microscope (Leitz) equipped with a motorized stage and focus control system and a Coolsnap-Pro color digital camera (Media Cybernetics, Silver Spring, Md., USA).

BrdU-Positive Cells

BrdU-positive cells in the DG of P15 mice were detected using a fluorescence microscope (Eclipse; objective: ×40, 0.75 NA; final magnification: ×400). Quantification of BrdU-labeled nuclei was conducted in every 6th section using a modified unbiased stereology protocol that has previously been reported as successfully quantifying BrdU labeling (Malberg et al., 2000; Kempermann and Gage, 2002; Tozuka et al., 2005). All BrdU labeled cells located in the granule cell and subgranular layers were counted in their entire z axis (1 µm steps) in each section. To avoid oversampling errors, nuclei intersecting the uppermost focal plane were excluded. The total number of BrdU labeled cells per animal was determined and multiplied by six to obtain the total estimated number of cells per DG.

Stereology of the DG

Unbiased stereology was performed on Hoechst-stained sections from P15 mice. The optical dissector method was used to obtain density, and Cavalieri principle was used to estimate volume (West and Gundersen, 1990). To include 15-20 sections, one every 6th section was selected, beginning at a random position within the first 6 sections. In order to obtain granule cell numerical density, counting frames (disectors) with a side length of 30 µm and a height of 10 µm spaced in a 100 µm square grid were systematically used. Granule cell nuclei were counted with a ×64 oil objective (1.4 NA). Granule cell nuclei intersecting the uppermost focal plane and intersecting the exclusion lines of the count frame were not counted. The neuron density (NV) is given by $$NV = (\Sigma Q \Sigma \text{dis}) V \text{dis}$$

where Q is the number of particles counted in the disectors, dis is the number of disectors and Vdis is the volume of the disector. For calculation of Vdis the disector height was corrected for section shrinkage in the z-plane (Dorph Petersen et al., 2001) according to the formula: h=counting thickness×(original thickness/measured thickness). The section thickness was measured during neuron counting at different random locations. In the analyzed sections, the mean section thickness was 16 µm (range: 12-18 µm). For volume (Vref) estimation with the Cavalieri principle, in each sampled section, the area of the granule cell layer was measured by tracing its contours. The volume of the granule cell layer (Vref) was estimated (West and Gundersen, 1990) by multiplying the sum of the cross sectional areas by the spacing T between sampled sections (180 µm). The total number (N) of granule cells was estimated as the product of Vref and the numerical density (NV).

$$N = NV \times V\text{ref}$$

Spine Density

In Golgi-stained sections from the DG of P15 mice, spines of granule cells were counted using a 100× oil immersion objective lens (1.4 NA). Spine density values were obtained from dendritic segments in the inner and outer half of the molecular layer. For each neuron, 2-3 segments were analyzed in the outer and inner half of the molecular layer, respectively. For each animal, spines were counted in at least 8 neurons. The length of each sampled dendritic segment was determined by tracing its profile and the number of spines was counted manually. The linear spine density was calculated by dividing the total number of spines by the length of the dendritic segment. Spine density was expressed as number of spines per 100 µm dendrite.

3.6 Western Blotting

In homogenates of the hippocampal formation of P15 mice, total proteins were obtained as previously described (Trazzi et al., 2011) and the levels of the following proteins were evaluated: BDNF, TrkB full length (TrkB-FL), phosphorylated TrkB (p-TrkB), the truncated form 1 of the TrkB receptor (TrkB-T1), phosphorylated ERK1 (p-ERK1), phosphorylated ERK2 (p-ERK2), ERK1, ERK2, synaptophysin (SYN), GAPDH and α-Tubulin using the antibodies reported in Table 1. Densitometric analysis of digitized images with ChemiDoc XRS+ was performed with Image Lab software (Bio-Rad Laboratories, Hercules, Calif., USA) and intensity for each band was normalized to the intensity of the corresponding GAPDH or α-Tubulin band.

3.7 Behavioral Testing

Morris Water Maze (MWM)

Mice were trained in the MWM task to locate a hidden escape platform in a circular pool, using a previously used protocol (Stagni et al., 2016), that was altogether based on a published protocol (Vorhees and Williams, 2006). The apparatus consisted of a large circular water tank (1.00 m diameter, 50 cm height) with a transparent round escape platform (10 cm$^2$). The pool was virtually divided into four equal quadrants identified as northeast, northwest, southeast, and southwest. The tank was filled with tap water at a temperature of 22±1.0° C. Mice are more prone to undergo hypothermia than rats and in the MWM hypothermia may cause a reduction in swimming speed (Iivonen et al., 2003). Evaluation of the swimming speed showed no speed differences across consecutive trials, suggesting that at this temperature mice did not undergo hypothermia (FIG. 9). This is consistent with evidence that a temperature of 22° C. is "high enough" to reduce stress and potential hypothermia and "low enough" to maintain the animals' motivation to escape the pool (Costa et al., 2010). The tank was filled with water up to 0.5 cm above the top of the platform and the water was made opaque with milk. The platform was placed in the tank in a fixed position (in the middle of the southwest quadrant). The pool was placed in a large room with various intra (squares, triangles, circles and stars) and extra-maze visual cues. Each mouse was tested in one session of 4 trial on the first day and in two sessions of 4 trials in the following 4 days with an inter-session interval of 45 min. A video camera was placed above the center of the pool and connected to a videotracking system (Ethovision 3.1; Noldus Information Technology B.V., Wageningen, Netherlands). Mice were released facing the wall of the pool from one of the following starting points: North, East, South, or West and allowed to search for up to 60 s for the platform. If a mouse did not find the platform, it was gently guided to it and allowed to remain there for 15 s. During the inter-trial time (10 s) mice were placed in an empty cage. For the learning phase, we evaluated the latency to find the hidden platform, time in periphery, percentage of time in periphery, path length, proximity to the platform, and swimming speed. Retention was assessed with one trial (probe trial), on the sixth day, 24 h after the last acquisition trial, using the same starting point for all mice. Mice were allowed to search for up to 60 s for the platform. For the probe trial, the latency of the first entrance in the former platform zone, the frequency of entrances in the former quadrant, the proximity to the former platform position (Gallagher's test), the percentage of time spent at the periphery (thigmotaxis), the swimming speed and the percentage of time spent in each quadrant were employed as measures of retention of acquired spatial preference. All experimental sessions were carried out between 9.00 am and 5.00 µm. The following number of mice were tested. Untreated euploid mice: n=19; untreated Ts65Dn mice: n=14; 7,8-DHF-treated euploid mice: n=17; 7,8-DHF-treated Ts65Dn mice: n=16. Three untreated euploid mice (yielding n=16), one 7,8-DHF-treated euploid mouse (yielding n=16) and one 7,8-DHF-treated Ts65Dn mouse (yielding n=15) were excluded from MWM analysis due to thigmotaxis for a whole recording session.

3.8 Statistical Analysis

Results are presented as mean±standard error of the mean (SE). Data were analyzed with the IBM SPSS 22.0 software. Statistical analysis was carried out using either a one-way ANOVA or a two-way ANOVA with genotype (euploid, Ts65Dn) and treatment (vehicle, 7,8-DHF) as factors. Post hoc multiple comparisons were carried out using the Fisher least significant difference (LSD) test. For the learning phase of the MWM test, statistical analysis was performed using a three-way mixed ANOVA, with genotype and treatment as grouping factors and days as a repeated measure. For the probe test of MWM, we used a two-way ANOVA with genotype and treatment as factors followed by the Fisher LSD post hoc test for the latency of the first entrance in the former platform zone, the frequency of entrances in the former quadrant, the proximity to the former platform position, the percentage of time spent at the periphery, and the swimming speed. For the percentage of time spent in quadrants, the percentage of time spent in the NW, NE and SE quadrants was compared to the percentage of time spent in the former platform quadrant (SW), respectively, with a paired-samples t-test. Based on the "Box plot" tool available in SPSS Descriptive Statistics we excluded from each analysis the extremes, i.e. values that were larger than 3 times the IQ range [x≥Q3+3*(IQ); x≤Q1−3*(IQ)]. The number of mice included and excluded in individual analyses is reported in Table 3. Figure legends report the number of mice used for statistical analysis. Tables 4-9 report the p values of the post-hoc LSD or paired-samples t-test for each analysis. A probability level of p≤0.05 was considered to be statistically significant.

Results

Effect of Treatment with 7,8-DHF on Proliferation, Differentiation and Maturation of Trisomic NPCs Confirming previous evidence (Trazzi et al., 2011; Trazzi et al., 2013), neural progenitor cells (NPCs) from the subventricular zone (SVZ) of neonate Ts65Dn mice exhibit impairment of proliferation rate (FIG. 1A). Cultures of trisomic NPCs were exposed to standard medium (vehicle) or standard medium plus different concentrations of 7,8-DHF, in order to establish whether treatment increases their proliferation rate. A one-way ANOVA showed a significant effect of treatment [F (5,12)=81.364, p≤0.001]. A post hoc LSD test showed that none of the tested concentrations was able to increase the proliferation rate of trisomic NPCs and that the highest concentration (10.0 μM) even reduced proliferation (FIG. 1B). In contrast, cells were highly responsive to the pro-proliferative action of 2 mM lithium (FIG. 1B). In addition to proliferation impairment, trisomic NPCs exhibit impairment in the acquisition of a neuronal phenotype and maturation, i.e. development of neuritic processes (Trazzi et al., 2011; Trazzi et al., 2013). In order to establish whether treatment favors neurogenesis, in cultures of NPCs under differentiating conditions we evaluated the percentage of cells positive to MAP2, a marker of cells with a neuronal phenotype, and of cells positive to Nestin, a marker of neural stem cells. A one-way ANOVA on the percentage of cells that were MAP2-positive and Nestin-negative (MAP2+/Nestin−) showed a significant effect of treatment [F(5,12)=9.354, p≤0.001]. A post-hoc LSD test showed that all drug concentrations caused a large increase in the percentage of MAP2+/Nestin− cells in comparison with cultures in the standard medium (FIG. 1C). Consistently with the lack of effect of treatment on the proliferation rate of NPCs (FIG. 1B) we found no change in the percentage of cells that were Nestin-positive and MAP2-negative (Nestin+/MAP2−; FIG. 1D). This evidence suggests that treatment does not affect the proliferation rate of neural stem cells but enhances the differentiation of their progeny into neurons. In order to establish the effect of 7,8-DHF on neuron maturation we evaluated the percentage of cells exhibiting neuritic processes in differentiating cultures of trisomic NPCs from the SVZ and from the subgranular zone (SGZ) of the dentate gyrus (DG), exposed to different concentrations of 7,8-DHF. A one-way ANOVA on the percentage of NPCs from the SGZ that exhibited neuritic processes showed a significant effect of treatment [F(5,12)= 4.336, p=0.017]. A post-hoc LSD test showed that concentrations higher than 1.1 μM increased the percentage of differentiating cells in comparison with cultures in the standard medium (FIG. 1E,F). A one-way ANOVA on the percentage of NPCs from the SVZ that exhibited neuritic processes showed a significant effect of treatment [F(5,12) =12.364, p≤0.001]. A post-hoc LSD test showed that doses higher than 0.3 μM increased the percentage of differentiating cells in comparison with cultures in the standard medium (FIG. 1G,H). Observation of FIG. 1F,H shows that effect of treatment on neuron maturation increased in a concentration-dependent manner. Evaluation of the number of apoptotic cells showed no effect of treatment (data not shown). Taken together these data show that 7,8-DHF does not increase the proliferation rate but fosters the process of neurogenesis and neuron maturation in cultures of NPCs.

Effect of Treatment with 7,8-DHF In Vivo: General Results

The Ts65Dn strain is characterized by a high mortality rate during gestation (Roper et al., 2006). For this reason, the number of Ts65Dn pups in a litter results approximately 30% instead of the theoretical value of 50%. Moreover, Ts65Dn mice exhibit a high mortality rate before weaning (Roper et al., 2006). This means that numerous litters are needed in order to obtain a sufficiently large number of Ts65Dn mice. In view of the fragility of this strain, we deemed it important to establish whether treatment with 7,8-DHF has adverse effects on the viability and growth of Ts65Dn mice. In the current study, treatment with either 7,8-DHF or vehicle began on postnatal day 3 (P3). All mice that survived in the P0 to P3 period entered this study, with no specific selection criteria. We found that 7.3% of the vehicle-treated mice and 5.6% of the 7,8-DHF-treated mice died before weaning, in the P6-P22 period. The similarity in the mortality rate across groups suggests that treatment has no adverse effects on the health of mice.

The body and brain weight of P15 and P45 mice were evaluated in order to establish the effect treatment on gross growth parameters. A two-way ANOVA on the body weight of P15 mice showed no genotype×treatment interaction [F(1,92)=0.63, p=0.431], no main effect of treatment but a main effect of genotype [F(1,92)=14.78, p≤0.001]. Post hoc LSD test confirmed well established evidence that Ts65Dn mice have a reduced body weight in comparison with euploid mice and showed that treatment did not further reduce the body weight of Ts65Dn mice (FIG. 2C). A two-way ANOVA on the brain weight of P15 mice showed no genotype×treatment interaction [F(1,92)=1.09, p=0.300], a main effect of genotype [F(1,92)=7.73, p=0.007] and a main effect of treatment [F(1,92)=6.18, p=0.015]. Post hoc LSD test showed that Ts65Dn mice had a reduced brain weight in comparison with euploid mice and that treatment did not cause a further brain weight reduction (FIG. 2D). On the contrary, treated euploid mice underwent a slight but significant brain weight reduction in comparison with their untreated counterparts (FIG. 2D).

A two-way ANOVA on the body weight of P45 mice showed no genotype×treatment interaction [F(1,62)=1.57, p=0.215], no main effect of treatment but a main effect of genotype [F(1,62)=4.98, p=0.029]. Post hoc LSD test showed that Ts65Dn mice retained a reduced body weight in comparison with euploid mice and that treatment did not further reduce their body weight (FIG. 2E). In contrast, treated euploid mice underwent a body weight reduction in comparison with their untreated counterparts (FIG. 2E). A two-way ANOVA on the brain weight of P45 mice showed no genotype×treatment interaction [F (1,62)=2.06, p=0.156], no main effect of either genotype or treatment. Post hoc LSD test showed that untreated Ts65Dn mice had a reduced brain weight in comparison with untreated euploid mice and that this difference disappeared in Ts65Dn mice treated with 7,8-DHF (FIG. 2F). Taken together these findings show that treatment with 7,8-DHF has no adverse effects on viability and body weight of Ts65Dn mice and that it has a positive impact on their brain weight.

Effect of Treatment with 7,8-DHF on Neural Precursor Proliferation in the Hippocampal Dentate Gyrus of Ts65Dn Mice Recent work has examined the effect of 7,8-DHF in models of Alzheimer disease. A dose of 5.0 mg/kg has been shown to have no toxic effects and to restore cognitive performance (Liu et al., 2010). In addition, this dose increases the proliferation rate of neural precursor cells of the DG (Liu et al., 2010). In order to establish whether this is the optimal dose for proliferation enhancement in Ts65Dn mice, we treated pups with vehicle, 2.5 mg/kg, 5.0 mg/kg or 10.0 mg/kg of 7,8-DHF in the period P3-P15. At the end of treatment, mice received one injection of BrdU and were killed after 2 h in order to examine the effect of treatment on proliferation rate. A one-way ANOVA on the number of BrdU-positive cells in the DG of Ts65Dn pups showed a significant effect of treatment [$F(3,20)=4.15$, $p=0.019$]. Post hoc LSD test showed that the lowest dose had no effect in comparison with vehicle-treated mice and that both the 5.0 mg/kg and the 10.0 mg/kg doses increased the number of BrdU-positive cells in Ts65Dn mice. In absolute terms, the 5.0 mg/kg dose had a higher pro-proliferative effect than the 10.0 mg/kg dose (FIG. 3A).

Based on the results reported above, all following experiments in vivo were carried out using a 5.0 mg/kg dose. In order to establish the effects of 7,8-DHF on proliferation rate of NPCs of the DG, Ts65Dn mice and their euploid littermates were daily injected with 5.0 mg/kg of 7,8-DHF in the period P3-P15. At the end of treatment, mice were injected with BrdU and the number of BrdU-positive cells in the SGZ of the DG was evaluated. A two-way ANOVA on the total number of BrdU-positive cells showed a genotype×treatment interaction [$F(1,19)=8.53$, $p=0.009$], a main effect of genotype [$F(1,19)=21.25$, $p\leq0.001$], but no effect of treatment. A post hoc Fisher LSD test showed that, in agreement with previous evidence (Bianchi et al., 2010b), untreated Ts65Dn mice had notably fewer proliferating cells in comparison with untreated euploid mice (total number per DG in Ts65Dn mice: n=7166±337, in euploid mice: n=10, 281±111). The number of proliferating cells in treated Ts65Dn mice underwent an increase (n=8963±449) and became statistically greater than that of their untreated counterparts, although it remained slightly lower in comparison with untreated euploid mice (FIG. 3B,C). Treatment had no effect on the number of NPCs in euploid mice (FIG. 3B,C). These results show that treatment in vivo, unlike in vitro, greatly enhances cell proliferation in trisomic mice, although the number of proliferating cells does not reach the same value as euploid mice.

Effect of 7,8-DHF on the Number of Granule Neurons in the Dentate Gyrus of Ts65Dn Mice In view of the treatment-induced increase in the proliferation potency of neural precursor cells of the DG, we expected this effect to lead to improvement/restoration of the defective cellularity that characterizes the DG of trisomic mice (Bianchi et al., 2010b). To clarify this issue, we stereologically evaluated the total number of granule cells in treated and untreated mice. A two-way ANOVA on total number of granule cells showed a genotype×treatment interaction [$F(1,13)=6.71$, $p=0.022$], but no main effect of either genotype or treatment A post hoc Fisher LSD test showed that untreated Ts65Dn mice had fewer granule neurons in comparison with euploid mice and that treatment caused a large increase in their number. Consequently, in treated Ts65Dn mice the number of granule cells became similar to that of untreated euploid mice (FIG. 4A,B). Unlike in Ts65Dn mice, in euploid mice treatment had no effect on total number of granule cells (FIG. 4A,B). These results show that neonatal treatment with 7,8-DHF restores the typical hypocellularity that characterizes the DG of trisomic mice.

Effect of 7,8-DHF on Dendritic Spine Density in the Dentate Gyrus of Ts65Dn Mice Spine density reduction is a typical feature of the trisomic brain (Benavides-Piccione et al., 2004; Guidi et al., 2013) that, in conjunction with hypocellularity, is thought to be a critical determinant of intellectual disability. In order to establish whether 7,8-DHF improves this defect, in Golgi stained brains we evaluated spine density in the dendritic arbor of granule neurons. Since no differences between spine density on proximal and distal dendritic branches were found data were pooled together. A two-way ANOVA on spine density showed a genotype×treatment interaction [$F(1,12)=13.23$, $p=0.003$], a main effect of genotype [$F(1,12)=19.93$, $p=0.001$] and a main effect of treatment [$F(1,12)=42.30$, $p\leq0.001$]. A post hoc Fisher LSD test showed that untreated Ts65Dn had a considerably reduced spine density in comparison with untreated euploid mice (FIG. 5C). After treatment with 7,8-DHF the number of spines of Ts65Dn mice underwent a notable increment and became similar to that of euploid mice (FIG. 5C), indicating that treatment fully rescues spine development. In euploid mice, treatment had no effect on spine density (FIG. 5C).

Effect of 7,8-DHF on Synaptophysin Levels in the Hippocampal Formation of Ts65Dn Mice Circuit formation is critically shaped in the early postnatal period throughout the brain. The trisomic brain is characterized by altered synaptic connectivity that, in conjunction with hypocellularity and dendritic pathology, largely contributes to impairment of signal processing (Bartesaghi et al., 2011). Synaptophysin (SYN) is a protein of the synaptic vesicles and is, therefore, a marker of synaptic terminals. To establish whether treatment with 7,8-DHF had an effect on synapse development, we examined the expression levels of SYN in the hippocampus of P15 mice.

A two-way ANOVA on the levels of SYN showed no interaction between genotype and treatment [$F(1,27)=0.82$, $p=0.372$], no main effect of genotype, but a main effect of treatment [$F(1,27)=6.62$, $p=0.016$]. Confirming previous evidence (Stagni et al., 2013), a post hoc Fisher LSD test showed that untreated Ts65Dn mice had reduced SYN levels in comparison with untreated euploid mice, although the difference was marginally significant, and that treatment with 7,8-DHF increased SYN levels that became similar to those of untreated euploid mice (FIG. 5D). An increase in SYN levels also took place in treated euploid mice in comparison with their untreated counterparts (FIG. 5D). These findings suggest that treatment with 7,8-DHF restores development of hippocampal synapses in Ts65Dn mice and enhances synaptic development in euploid mice.

Effect of 7,8-DHF on the BDNF-TrkB Receptor System in the Hippocampal Formation of Ts65Dn Mice BDNF signaling is elicited when it binds to TrkB, resulting in the receptor dimerization and autophosphorylation. TrkB, the high affinity receptor of BDNF, and BDNF are essential for normal brain function (Bibel et al., 1999). The TrkB full-length receptor (TrkB-FL) possesses an intracellular tyrosine kinase domain and is considered to mediate the crucial effects of BDNF. By contrast, the truncated form 1 of the TrkB receptor (TrkB-T1) lacks tyrosine kinase activity. It mediates inositol-1,4,5-trisphosphate-dependent calcium release (Rose et al., 2003). We examined the protein levels of BDNF and TrkB receptors in the hippocampus of P15 euploid and Ts65Dn mice in order to establish the effect of genotype and treatment on the BDNF-TrkB system.

A two-way ANOVA on the BDNF levels showed no genotype×treatment interaction [$F(1,48)=0.86$, $p=0.359$], a main effect of treatment [$F(1,48)=8.76$, $p=0.005$], but no effect of genotype. A post hoc Fisher LSD test showed that Ts65Dn mice had similar BDNF protein levels as euploid mice (FIG. 6B). Treatment with 7,8-DHF caused a reduction in BDNF levels both in euploid and Ts65Dn mice although the difference was statistically significant for the latter only (FIG. 6B). A two-way ANOVA on the levels of TrkB-FL receptor showed no genotype×treatment interaction [$F(1,45)=2.17$, $p=0.148$], a main effect of genotype [$F(1,45)=5.71$, $p=0.021$] and no effect of treatment. A post hoc Fisher LSD test showed no difference between untreated euploid and Ts65Dn mice in the levels of TrkB-FL (FIG. 6A,C). In Ts65Dn, but not in euploid mice, treatment with 7,8-DHF caused a reduction in the levels of TrkB-FL (FIG. 6A,C). A two-way ANOVA on the levels of the phosphorylated form of TrkB receptor (p-TrkB-FL) showed no genotype×treatment interaction [$F(1,39)=0.03$, $p=0.865$], a main effect of treatment [$F(1,39)=10.88$, $p=0.002$] but no main effect of genotype. A post hoc Fisher LSD test showed that in untreated Ts65Dn mice the levels of p-TrkB-FL were similar to those of euploid mice. In both genotypes, treatment with 7,8-DHF caused an increase in the levels of p-TrkB-FL (FIG. 6A,D). A two-way ANOVA on the levels of the TrkB-T1 receptor showed a genotype×treatment interaction [$F(1,47)=6.04$, $p=0.018$], but no main effect of either treatment or genotype. A post hoc Fisher LSD test showed that untreated Ts65Dn mice has similar levels of TrkB-T1 as untreated euploid mice. Treated Ts65Dn mice underwent a reduction in the levels of TrkB-T1 in comparison with their untreated counterparts and untreated euploid mice (FIG. 6A,E).

The activation of the TrkB-FL receptor allows its interaction with molecules that further interact and modify downstream targets, including the RAS/ERK signaling pathway. Since RAS/ERK signaling is involved in cell proliferation and differentiation, we examined the effects of treatment on the activation of ERK1/2 in hippocampal homogenates of Ts65Dn and euploid mice. A two-way ANOVA on p-ERK1 levels showed no genotype×treatment interaction [$F(1,29)=0.78$, $p=0.385$], but a main effect of genotype [$F(1,29)=7.21$, $p=0.012$] and of treatment [$F(1,29)=4.64$, $p=0.040$]. Post-hoc Fisher LSD test showed that treated Ts65Dn mice underwent an increase in p-ERK1 levels in comparison with untreated Ts65Dn mice as well as untreated euploid mice (FIG. 6F). A two-way ANOVA on p-ERK2 levels showed no genotype×treatment interaction [$F(1,29)=1.73$, $p=0.199$], a main effect of genotype [$F(1,29)=8.92$, $p=0.006$] but no main effect of treatment. Post-hoc Fisher LSD test showed that treated Ts65Dn mice underwent an increase in p-ERK2 levels in comparison with untreated euploid mice (FIG. 6F). A two-way ANOVA on the levels of ERK1 showed no genotype×treatment interaction [$F(1,28)=0.815$, $p=0.374$] and no main effect of either treatment or genotype. Post-hoc Fisher LSD test showed that treated Ts65Dn mice underwent an increase in ERK1 levels in comparison with untreated Ts65Dn mice (FIG. 6G). A two-way ANOVA on the levels of ERK2 showed no genotype×treatment interaction [$F(1,30)=0.065$, $p=0.801$], no main effect of genotype, but a main effect of treatment [$F(1,30)=13.76$, $p=0.001$]. Post-hoc Fisher LSD test showed that Ts65Dn mice treated with 7,8-DHF underwent an increase in ERK2 levels in comparison with their untreated counterparts and untreated euploid mice (FIG. 6G). An increase in ERK2 levels also took place in treated euploid mice in comparison with their untreated counterparts (FIG. 6G). There is evidence that ERK2 is approximately four time more abundant than ERK1 in various brain regions and that alteration of the stoichiometry of the two isoform of ERK may have adverse effects (Lefloch et al., 2008). Therefore, we examined the relative abundance of ERK1/ERK2 and p-ERK1/ERK2 in treated and untreated mice. We found that in the hippocampal region of untreated euploid and Ts65Dn mice the ratio between ERK2 and ERK1 was approximately 3:1 and the ratio between p-ERK2 and p-ERK1 was approximately 2:1 (Table 10). Although in absolute terms treatment increased the levels of ERK1/2 and p-ERK1/2 in Ts65Dn mice (FIG. 6F,G), it did not affect their stoichiometry (Table 10).

Effect of 7,8-DHF on Hippocampus-Dependent Learning and Memory

At the age of P45 (an age approximately corresponding to adolescence), mice can be behaviorally tested with tasks that explore hippocampus-dependent learning and memory (Stagni et al., 2016). In order to establish whether the neuroanatomical effects of 7,8-DHF are functionally effective, we treated euploid and Ts65Dn mice from P3 to P45-50 and examined their behavior with the Morris Water Maze (MWM) test, a test that is classically used in trisomic mice to assess the effects of genotype and/or treatment on memory.

The learning phase of the test lasted 5 days and on day six mice were subjected to the probe test in order to evaluate spatial memory. For the learning phase, the following variables were evaluated: escape latency, time in periphery, percentage of time in periphery, path length, proximity, and swimming speed. We carried out a three-way mixed ANOVA for all variables followed by post-hoc Fisher LSD test. Results of ANOVA are reported hereafter and results of the post-hoc test are summarized in Table 2.

A three-way mixed ANOVA on escape latency, with genotype and treatment as grouping factors and day as a repeated measure revealed no effect of genotype×treatment×day [$F(4,228)=1.52$, $p=0.196$]. We found a genotype×day interaction [$F(4,228)=3.10$, $p=0.016$], a treatment×day interaction [$F(4,228)=2.77$, $p=0.028$], no genotype×treatment interaction [$F(1,57)=0.03$, $p=0.874$], a main effect of genotype [$F(1,57)=42.58$, $p\le0.001$], a main effect of treatment [$F(1,57)=10.14$, $p=0.002$], and a main effect of day [$F(4,228)=21.75$, $p\le0.001$]. While euploid mice exhibited a fast learning improvement with time, untreated Ts65Dn mice exhibited a very scarce learning improvement and the latency to reach the platform did not decrease throughout the test (FIG. 7A, Table 2). In contrast, Ts65Dn mice treated with 7,8-DHF showed a learning improvement and, save for day 3, their performance was not statistically different from that of untreated euploid mice (FIG. 7A, Table 2). In euploid mice treated with 7,8-DHF the latency was reduced in comparison with that of untreated euploid mice (FIG. 7A), although the difference was statistically significant on day 2 only (Table 2).

A three-way mixed ANOVA on the time spent at the periphery zone (thigmotaxis), with genotype and treatment as grouping factors and day as a repeated measure revealed an effect of genotype×treatment×day [$F(4,228)=2.88$, $p=0.023$]. We found no genotype×day interaction [$F(4,228)=0.99$, $p=0.412$], a treatment×day interaction [$F(4,228)=3.31$, $p=0.012$], no genotype×treatment interaction

[F(1,57)=0.001, p=0.992], a main effect of genotype [F(1, 57)=19.63, p≤0.001], a main effect of treatment [F(1,57)=8.07, p=0.006], and a main effect of day [F(4,228)=27.72, p≤0.001]. A post-hoc Fisher LSD test showed that while untreated Ts65Dn mice spent more time at the periphery than untreated euploid mice, Ts65Dn mice treated with 7,8-DHF spent a similar time as euploid mice (FIG. 7B, Table 2), suggesting an improvement in searching strategy. A reduction in thigmotaxis was also shown by euploid mice treated with 7,8-DHF.

A three-way mixed ANOVA on the percentage of time spent at the periphery, with genotype and treatment as grouping factors and day as a repeated measure revealed an effect of genotype×treatment×day [F(4,228)=3.01, p=0.019]. We found a genotype×day interaction [F(4,228)=2.47, p=0.045], a treatment×day interaction [F(4,228)=7.76, p≤0.001], no genotype×treatment interaction [F (1,57)=1.48, p=0.229], a main effect of genotype [F(1,57)=11.71, p=0.001], a main effect of treatment [F(1,57)=8.04, p=0.006], and a main effect of day [F(4,228)=23.88, p≤0.001]. Post-hoc Fisher LSD test showed that the time spent at the periphery by untreated Ts65Dn mice, expressed as percentage of the total latency, was similar to that of untreated euploid mice (FIG. 7C, Table 2). This means that the proportion of time spent at the periphery and outside the periphery was similar in euploid and Ts65Dn mice. Since in Ts65Dn mice the total latency to reach the platform was longer than in euploid mice, this means that Ts65Dn mice spent more time at the periphery as well as swimming outside the periphery, which implies that their longer escape latency can be attributed to both higher thigmotaxis levels and poorer spatial learning. In treated Ts65Dn mice the percentage of time in thigmotaxis underwent a reduction and on day 5 it was significantly different in comparison with their untreated counterparts (FIG. 7C, Table 2), suggesting an improvement in spatial learning.

A three-way mixed ANOVA on path length, with genotype and treatment as grouping factors and day as a repeated measure revealed no effect of genotype×treatment×day [F(4, 228)=2.09, p=0.082]. We found a genotype×day interaction [F(4,228)=7.80, p≤0.001], no treatment×day interaction [F(4,228)=0.54 p=0.707], no genotype×treatment interaction [F(1,57)=0.05, p=0.819], no main effect of genotype, no main effect of treatment but a main effect of day [F(4,228)=43.74, p≤0.001]. In all groups, the path length decreased from day 1 to day 5 (FIG. 7D). In untreated Ts65Dn mice, the reduction was smaller than in untreated euploid mice and on day 5 their path length was significantly greater in comparison with untreated euploid mice (FIG. 7D, Table 2). In contrast, on day 5 the path length of treated Ts65Dn mice was shorter in comparison with their untreated counterparts and equal to that of treated and untreated euploid mice, suggesting an improvement in searching strategy.

A three-way mixed ANOVA on proximity to the former platform position (Gallagher's test; proximity), with genotype and treatment as grouping factors and day as a repeated measure revealed an effect of genotype×treatment×day [F(4, 228)=2.59, p=0.038]. We found a genotype×day interaction [F(4,228)=3.93, p=0.004], a treatment×day interaction [F(4, 228)=4.79, p≤0.001], no genotype×treatment interaction [F(1,57)=1.12, p=0.295], a main effect of genotype [F(1,57)=9.66, p=0.003], a main effect of treatment [F (1,57)=12.91, p=0.001], and a main effect of day [F(4,228)=13.39, p≤0.001]. FIG. 7E shows that while in untreated euploid mice the distance from the platform position decreased from day 1 to day 5, untreated Ts65Dn mice underwent no improvement. In contrast, treated Ts65Dn mice underwent an improvement and on day 5 their distance from the platform was significantly reduced in comparison with their untreated counterparts and similar to that of untreated and treated euploid mice (FIG. 7E, Table 2).

A three-way mixed ANOVA on swimming speed, with genotype and treatment as grouping factors and day as a repeated measure revealed an effect of genotype×treatment×day [F(4,228)=3.20, p=0.014]. We found no genotype×day interaction [F(4,228)=0.71, p=0.584], no treatment×day interaction [F(4,228)=1.98, p=0.098], no genotype×treatment interaction [F(1,57)=0.09, p=0.760], a main effect of genotype [F(1,57)=5.27, p=0.025], no main effect of treatment, but a main effect of day [F(4,228)=20.05, p≤0.001]. A post-hoc Fisher LSD test showed that in untreated Ts65Dn mice the swimming speed was similar to that of untreated euploid mice and treated euploid and Ts65Dn mice throughout the learning phase (FIG. 7F, Table 2), suggesting that their longer escape latency was not due to a speed reduction. Treated Ts65Dn mice had a reduced speed in comparison with untreated euploid mice on days 1, 2, and 3 but similar to that of euploid mice on days 4 and 5, suggesting that their reduced escape latency was not due to an improvement in swimming speed. Treated euploid mice had a reduced speed in comparison with untreated euploid mice on day 1, but a similar speed on days 2-5 (FIG. 7F, Table 2).

In the probe test, we considered the following parameters as an index of spatial memory: i) latency to enter the former platform zone (latency), ii) frequency of entrances in the former quadrant (frequency), iii) proximity to the former platform position (Gallagher's test; proximity), iv) percentage of time spent at the periphery (thigmotaxis); v) swimming speed; vi) percentage of time spent in each quadrant. A two-way ANOVA on the latency showed no genotype×treatment interaction [F(1,57)=0.87, p=0.356], but a main effect of genotype [F (1,57)=10.24, p=0.002] and a main effect of treatment [F(1,57)=4.60, p=0.036]. Post-hoc Fisher LSD test showed that untreated Ts65Dn mice exhibited a larger latency than euploid mice and that treatment caused a notable reduction in their latency that became similar to that of untreated euploid mice (FIG. 8A). A two-way ANOVA on the frequency showed no genotype×treatment interaction [F(1,57)=0.001, p=0.992], but a main effect of genotype [F(1,57)=10.06, p=0.002] and a main effect of treatment [F(1,57)=7.46, p=0.008]. Post-hoc Fisher LSD test showed that untreated Ts65Dn mice exhibited a reduced frequency of entrances than euploid mice. In treated Ts65Dn mice there was a notable increase in the frequency that became similar to that of untreated euploid mice (FIG. 8B). A large increase in the frequency of entrances took place in treated euploid mice (FIG. 8B). This effect is in line with the reduction in the percentage of time they spent at the periphery (FIG. 8F). A two-way ANOVA on the proximity showed no genotype×treatment interaction [F(1,57)=1.60, p=0.211], but a main effect of genotype [F(1,57)=4.81, p=0.032] and a main effect of treatment [F(1,57)=7.05, p=0.010]. Post-hoc Fisher LSD test showed that untreated Ts65Dn mice swam at a larger distance from the former platform zone in comparison with untreated euploid mice (FIG. 8C). Treated Ts65Dn mice swam closer to the former platform zone and their performance became similar to that of untreated euploid mice (FIG. 8C).

A two-way ANOVA on the percentage of time spent at the periphery showed no genotype×treatment interaction [F(1, 57)=0.62, p=0.436], no main effect of genotype but a main effect of treatment [F(1,57)=12.03, p=0.001]. Post-hoc Fisher LSD test showed that in untreated Ts65Dn mice the percentage of time spent at the periphery was similar to that of untreated euploid mice (FIG. 8D). The finding that Ts65Dn mice spent the same proportion of time in and outside the periphery as euploid mice suggests that their longer escape latency (FIG. 8A) can be attributed to poorer spatial memory for the former platform location. In treated Ts65Dn mice the percentage of time spent in the periphery was reduced in comparison with their untreated counterparts (FIG. 8D), suggesting an improvement in searching strategy. A reduction in the percentage of time at the periphery was also exhibited by treated vs. untreated euploid mice (FIG. 8D).

A two-way ANOVA on the swimming speed showed no genotype×treatment interaction [$F(1,57)=0.44$, $p=0.511$], no main effect of genotype and no main effect of treatment and post-hoc Fisher LSD test showed no differences between groups (FIG. 8E).

A paired samples t-test showed that untreated Ts65Dn mice exhibited no differences in the time spent in the former platform quadrant in comparison with the other quadrants (FIG. 8F). In contrast, treated Ts65Dn mice spent significantly more time in the former platform quadrant in comparison with the NE quadrant [$t(14)=2.49$; $p=0.026$] and with the SE quadrant, although the latter difference was only marginally significant [$t(14)=2.05$; $p=0.059$]. Untreated euploid mice spent significantly more time in the former platform quadrant in comparison with the NE [$t(15)=3.09$; $p=0.008$] and SE quadrant [$t(15)=2.16$; $p=0.047$] quadrants. Likewise, treated euploid mice spent significantly more time in the former platform quadrant in comparison with the NE [$t(15)=3.85$; $p=0.002$] and SE quadrant [$t(15)=6.02$; $p\leq0.001$] quadrants (FIG. 8F).

Taken together, these results are in agreement with a number of studies showing that Ts65Dn mice are impaired in spatial learning and memory. In treated Ts65Dn mice, the parameters of the learning phase tended to ameliorate day by day, although not to a significant level, but at day 5 the performance of Ts65Dn mice underwent a significant improvement in comparison with their untreated counterparts and was similar to that of untreated euploid mice. Importantly, in the probe test the behavior of treated Ts65Dn mice was similar to that of untreated euploid mice suggesting memory restoration.

Treatment with the BDNF Mimetic 7,8-DHF Positively Impacts the Major Defects of Hippocampal Development in Ts65Dn Mice Although neonate Ts65Dn mice exhibited similar BDNF levels as those of euploid mice, treatment with the BDNF mimetic 7,8-DHF resulted in the recovery of the major trisomy-linked developmental defects, i.e. neurogenesis reduction and dendritic pathology, which is in line with the key role played by BDNF in brain development. In particular, we found that treatment with 7,8-DHF increased the of dividing cells in the SGZ of Ts65Dn mice. While in untreated Ts65Dn mice the number of proliferating cells was—30% in comparison with untreated euploid mice, in treated Ts65Dn mice their number became—13% (see FIG. 3C), indicating that, although 7,8-DHF does not fully rescue NPC proliferation, it causes a large improvement. It is of interest to observe that in cultures of NPCs 7,8-DHF failed to increase cell proliferation (FIG. 1B), although it induced a robust effect on differentiation and maturation. This suggests that 7,8-DHF does not directly induce pro-proliferative signals in NPCs but that its pro-proliferative effects require the presence of other elements of the neurogenic niche (non-cell autonomous effect). Importantly, although the number of dividing cells in the SGZ of Ts65Dn mice was not fully rescued, total granule cell number was fully restored. This result may be explained by an effect of treatment on the process of phenotype acquisition, with a shift in the relative number of cells destined to become neurons. This conclusion is in line with the observation that in cultures of trisomic NPCs treatment largely increased the number of trisomic cells that differentiated into neurons (FIG. 1C).

It was additionally found that 7,8-DHF favors the process of neurite elongation in trisomic neurons of both the SVZ and SGZ, indicating a positive impact of treatment on the process of neuron maturation. The granule neurons of Ts65Dn mice aged 15 days exhibited spine density reduction, indicating impairment in the process of spinogenesis from the earliest phases of hippocampal development. As each dendritic spine receives at least one excitatory input, a reduction in the number of spines of granule neurons implies a reduction in the number of excitatory terminals and, consequently, reduced complexity of hippocampal circuitry. Evaluation of the levels of the presynaptic protein SYN in Ts65Dn mice showed that the counterpart of the spine density reduction was a reduction in SYN levels. Treatment with 7,8-DHF fully restored the reduced number of dendritic spines of Ts65Dn mice as well as SYN levels, suggesting a positive impact on the overall connectivity of the DG.

Conflicting results are reported in the literature regarding the pro-proliferative effect of the BDNF-TrkB system in different species and cellular systems (Foltran and Diaz, 2016; Vilar and Mira, 2016). Many studies suggest that BDNF fosters neurogenesis and neuron maturation but not proliferation of NPCs. Our results suggest that in Ts65Dn mice activation of the TrkB receptor enhances NPCs proliferation, in addition to neurogenesis and neuron maturation. Although the effect on proliferation was less prominent than the effect on neurogenesis and neuron maturation, the outcome was restoration of the defective cellularity in the granule layer of the DG. It is of interest to observe that some of the neurogenesis-enhancing therapies attempted so far in mouse models of DS may present caveats for human use due to the risk of uncontrolled proliferation in peripheral tissues and, thus, a cancerogenic effect (Bartesaghi et al., 2011; Gardiner, 2015). The finding that 7,8-DHF, in spite of its relatively moderate pro-proliferative activity, is able to restore the final number of granule neurons may render this molecule a good candidate for therapy in DS.

Treatment with 7,8-DHF rescues hippocampus-dependent behavior in Ts65Dn mice Hippocampus-dependent learning and memory impairment is a consistent feature of DS and the Ts65Dn mouse model (Demas et al., 1996; Carlesimo et al., 1997; Vicari et al., 2000; Belichenko et al., 2007; Salehi et al., 2009). This defect is attributable to hippocampal hypocellularity, altered neuronal maturation and altered connectivity. The granule cells of the DG are the first element of the hippocampal trisynaptic circuit, a circuit whose function is fundamental for long-term memory. The dendrites of the granule cells receive their major input from the entorhinal cortex that represents an interface between the hippocampal formation and the rest of the brain. Signals from polymodal association cortices sent by the entorhinal cortex to the DG are processed by the trisynaptic circuit and then sent back to the entorhinal cortex. We found here that in Ts65Dn mice treated with 7,8-DHF there was an improvement in hippocampus-dependent learning and a rescue in spatial memory, as assessed in the probe test, indicating that the effects of treatment on the hippocampal defects that characterize the trisomic condition translate into a behavioral benefit. It remains to be established whether after treatment cessation these effects are retained at further life stages.

Activation of the TrkB Receptor by 7,8-DHF Enhances the Activity of TrkB Receptor-Dependent Signaling In the hippocampus of P15 Ts65Dn mice we found normal levels of BDNF, TrkB-FL, and TrkB-T1 receptors. Results showed reduced levels of BDNF and TrkB-FL receptor in Ts65Dn mice after thirteen days of treatment with 7,8-DHF, suggesting a compensatory reduction of their transcription and/or an increase in their degradation. There is evidence that treatment with BDNF or the BDNF mimetic 7,8-DHF elicits TrkB receptor ubiquitination and degradation (Liu et al., 2016). This mechanism may account for the reduction in the protein levels of the TrkB receptor observed here in treated Ts65Dn mice. The absence of a similar reduction in treated euploid mice suggests that the mechanisms underlying degradation of the TrkB receptor may be more powerful in the trisomic brain. It must be noted that, although treatment induced an overall reduction in TrkB receptor levels, its phosphorylation increased, indicating that treatment enhances TrkB-dependent signaling.

The cellular effects of the BDNF-TrkB system are mediated by three major pathways, among which the RAS/MEK/ERK pathway appears to be involved in key developmental processes such as differentiation and survival (Arevalo and Wu, 2006). We found that in treated Ts65Dn mice there was an increase in the levels of p-ERK1 and p-ERK2, which is consistent with the treatment-induced phosphorylation increase of the TrkB receptor. ERK activity is required for cell proliferation (Lefloch et al., 2008), and there is evidence that the BDNF-TrkB signaling-induced increase in spine density of hippocampal pyramidal neurons requires ERK1/2 activation (Alonso et al., 2004). This evidence strongly suggests that the increased activity of ERK1/2 following treatment with 7,8-DHF may represent a key contributor to the rescue of the key processes of hippocampal development in Ts65Dn mice.

Although much is now known regarding the role of ERK1/2, the mechanisms underlying their expression still need to be elucidated (Busca et al., 2016). We found here that treatment with 7,8-DHF increased both ERK1 and ERK2 levels. A recent study shows that the ratio between total ERK1 and ERK2 protein levels in different mouse brain regions is about 1:4, that the same ratio holds for p-ERK1/2 and that derangement of these ratios has adverse effects on the brain (Lefloch et al., 2008). Importantly, in Ts65Dn mice, treatment caused an increase in ERK1/2 and p-ERK1/2 but their ratios remained similar to those of their untreated counterparts. This indicates that treatment enhances the activity of ERK1/2 without disrupting the important balance between the two ERK isoforms.

Treatment with 7,8-DHF has No Adverse Effects on Viability and Growth of Ts65Dn Mice Previous evidence showed that chronic treatment with 7,8-DHF has no toxic effects (Liu et al., 2016). In agreement with this evidence, we found no effect of treatment on mice viability. There is evidence that in rodents treatment with BDNF causes a reduction in food intake and that activation of muscular TrkB by 7,8-DHF regulates energy metabolism in muscles (Gray et al., 2006; Chan et al., 2015). Conversely, rodent models with a reduction in BDNF-TrkB signaling exhibit hyperphagia and obesity (Gray et al., 2006). We found that a relatively short treatment with 7,8-DHF (13 days: from P3 to P15) as well as a more prolonged treatment (42-47 days: from P3 to P45-50) did not cause a body weight reduction in Ts65Dn mice. In addition, we did not found an adverse effect of treatment on the brain weight of Ts65Dn mice, but rather, a positive effect on brain growth. From these findings it appears that a chronic treatment with 7,8-DHF has a safe profile on the general health of Ts65Dn mice.

Conclusions 7,8-DHF is a molecule that binds to the TrkB receptor and causes its dimerization and autophosphorylation, thereby mimicking the actions of BDNF. This binding replicates many actions of BDNF such as those on neurogenesis, neuron survival, learning and memory, and synaptogenesis. This study provides novel evidence that treatment with 7,8-DHF during the neonatal period restores the major trisomy-linked neurodevelopmental defects in the hippocampus of a mouse model of DS.

Neurogenesis in the hippocampal formation, one of the most important brain regions involved in pattern separation/completion and memory formation (Rolls, 2016), is severely disrupted in fetuses with DS (Contestabile et al., 2007; Guidi et al., 2008). Neurogenesis impairment is likely to account for hippocampal hypotrophy and for impairment of hippocampus-dependent memory functions in children with DS (Vicari et al., 2000). The current results suggest that therapy with the BDNF mimetic 7,8-DHF may represent a possible strategy for improving brain development and memory in children, and possibly in adults, with DS. In spite of the intrinsic limitations of mouse models, our work suggests that it is possible to restore trisomy-linked developmental deficits by pharmacologically targeting the TrkB receptor with a naturally occurring flavonoid. As pointed out in the Introduction, the problem of pharmacological interventions is that they are, in most cases, Janus-faced. The positive effects of many of the drugs used so far in DS models are the "good face" of Janus but the "bad face" deals with the far-from-irrelevant issue of safety. Flavonoids are compounds naturally present in vegetables and fruits (Rendeiro et al., 2015) and exert beneficial effects on the brain in health and disease (Spencer, 2008; Williams and Spencer, 2012). Considering that treatment with 7,8-DHF has no toxic effects in wild type mice (Liu et al., 2013) and in Ts65Dn mice (current study), our results suggest that early treatment with 7,8-DHF may represent a therapeutic strategy alternative to other drugs and with a good translational potential for improving brain development in DS.

Effect of Prenatal Treatment with 7,8-DHF: Prenatal Treatment with 7,8-DHF Restores Neurogenesis in the Forebrain of the Ts65Dn Model of DS 1. Colony Ts65Dn mice were generated by mating B6EiC3Sn a/A-Ts(17^16)65Dn females with C57BL/6JEiJ×C3H/HeSnJ (B6EiC3Sn) F1 hybrid males. This parental generation was provided by Jackson Laboratories (Bar Harbor, Me., USA). Animals were genotyped as previously described (Reinholdt et al., 2011). The animals' health and comfort were controlled by the veterinary service. The day of birth was designed as postnatal day (P) zero. A total of 42 P2 mice entered the study (vehicle-treated euploid mice n=17; vehicle-treated Ts65Dn mice n=11; 7,8-DHF-treated euploid mice n=5; 7,8-DHF-treated Ts65Dn mice n=9). The breeders had access to water and food ad libitum and lived in a room with a 12:12 h light/dark cycle. Experiments were performed in accordance with the European Communities Council Directive of 24 Nov. 1986 (86/609/EEC) for the use of experimental animals and were approved by Italian Ministry of Public Health (813/2016-PR). In this study, all efforts were made to minimize animal suffering and to keep the number of animals used to a minimum.

2. Experimental Protocol

Ts65Dn females (n=4) were bred C57BL/6JEi× C3SnHeSnJ (B6EiC3) F1 males (n=4). Conception was determined by examining the vaginal plug. Pregnant females received a daily subcutaneous injection of either 7,8-DHF (Sigma-Aldrich) in PBS with 2% DMSO (dose: 5 mg/kg) or vehicle from the embryonic (E) day 10 (E10) to the day of delivery (E20/21). In order to maintain the same genetic background, females that had received vehicle were subsequently bred with the same males and treated with 7,8-DHF. On postnatal day 2 (P2) the progeny of 7,8-DHF-treated and vehicle-treated females received an intraperitoneal injection (150 μg/g body weight) of BrdU (Sigma) in 0.9% NaCl solution and were killed after 2 h (on P2; 4-8 animals for each group). Vehicle-treated females and their progeny will be called hereafter untreated mice. The body weight of P2 mice was recorded prior to sacrifice. After sacrifice, brain was excised and weighed. The number of animals used for the evaluated variables is reported in the figure legends. Note that in the results described hereafter data of treated euploid mice have been left out.

3. Histological procedures

P2 animals were decapitated and the brain was removed. The rostral brain (forebrain plus mesencephalon) was separated from the hindbrain (cerebellum plus pons and medulla). The rostral brain was cut along the midline and fixed by immersion in Glyo-Fixx as previously described (Bianchi et al., 2010). The rostral brain was embedded in paraffin and cut in series of 8-μm-thick coronal sections that were attached to poly-lysine coated slides. The brain coordinates (BC) indicated below refer to the coordinates for P0 mice reported in the "Atlas of the developing mouse brain" (Paxinos et al., 2007).

4. Immunohistochemistry

One of 20 sections (n=8-10) from the beginning to the end of the hippocampal formation were subjected to double-fluorescence immunohistochemistry for BrdU and NeuN. Sections were incubated overnight at 4° C. with a primary antibody, rat monoclonal anti-BrdU antibody (AbD Serotec), diluted 1:100 in 0.1% Triton X-100 in PBS and either mouse monoclonal anti-NeuN (Millipore Bioscience Research Reagents) diluted 1:400 in 0.1% Triton X-100 in PBS. Sections were then washed in 0.1% Triton X-100 in PBS for 40 min and incubated for 2 h with a Cy3-conjugated anti-rat IgG (1:200; Jackson Immunoresearch) secondary fluorescent antibody for BrdU immunohistochemistry and FITC-conjugated anti-mouse IgG (1:200; Jackson Immunoresearch) for NeuN immunohistochemistry.

5. Measurements

Image acquisition. Immunofluorescence images were taken with a Nikon Eclipse TE 2000-S inverted microscope (Nikon Corp., Kawasaki, Japan), equipped with a Nikon digital camera DS 2MBWc. Measurements were carried out using the software Image Pro Plus (Media Cybernetics, Silver Spring, Md. 20910, USA).

Number of BrdU-Positive Cells.

BrdU-positive cells were sampled in the caudal subventricular zone (SVZ) of the lateral ventricle overlying the dentate gyrus and from the subgranular zone (SGZ) of the dentate gyrus (FIG. 10A). The caudal SVZ is the region that stretches from the beginning to the end of the hippocampal formation (BC: 3.27-4.84 mm). Since different regions of the ventricular zone (VZ) and SVZ give origin to neurons destined to different telencephalic areas (Brazel et al., 2003), we evaluated the effects of treatment both in the dorsal and lateral part of the SVZ (FIG. 10B). For cell counting, an area was traced enclosing the whole SVZ and all cells in this area were counted. While at later life stages, neural progenitor cells are only present in the SGZ of the dentate gyrus, in P2 pups proliferating cells can be detected in the perspective molecular layer and hilus. Therefore, cells were counted within a manually-traced area enclosing the whole dentate gyrus (FIG. 10B). This region will be called hereafter SGZ. Quantification of BrdU-labeled nuclei was conducted in every 20th section. The total number of BrdU labeled cells in the SVZ and SGZ was estimated by multiplying the number counted in the sampled sections by the inverse of the section sampling fraction (ssf=$\frac{1}{20}$).

6. Statistical Analysis

Results are presented as mean±standard error of the mean (SE). Data were analyzed with the IBM SPSS 22.0 software. Statistical analysis was carried out using a two-way ANOVA with genotype (euploid, Ts65Dn) and treatment (vehicle, 7,8-DHF), as factors. Post hoc multiple comparisons were carried out using the Fisher least significant difference (LSD) test. Based on the "Box plot" tool available in SPSS Descriptive Statistics we excluded from each analysis the extremes, i.e. values that were larger than 3 times the IQ range [x≥Q3+3*(IQ); x≤Q1−3*(IQ)]. Figure legends report the number of mice used for statistical analysis. A probability level of p≤0.05 was considered to be statistically significant.

Results

Effect of Treatment with 7,8-DHF on the Number of Proliferating Cells in the SVZ of Ts65Dn Mice The effect of genotype and treatment on the number of neural precursor cells with immunohistochemistry for BrdU, a marker that is incorporated by proliferating cells during the S-phase of the cell cycle, was assessed. Observation of FIG. 11A,B shows that in the SVZ of untreated Ts65Dn mice there were patently fewer BrdU-positive cells in comparison with euploid mice. Quantification of total cell number showed that while in the SVZ of Ts65Dn mice there were approximately 22500 BrdU-positive cells, in the SVZ of euploid mice there were approximately 32300 (FIG. 11D). These figures indicate that the number of proliferating cells in P2 Ts65Dn mice was −30% in comparison with euploid mice. Observation of FIG. 11B,C shows that embryonically-treated Ts65Dn mice had patently more BrdU-positive cells in comparison with their untreated counterparts. Quantification of total cell number showed that in the SVZ of treated Ts65Dn mice there were approximately 33900 BrdU-positive cells (FIG. 11D). These figures indicate that treated Ts65Dn mice underwent an increase in cell number of +50%. A comparison of treated Ts65Dn and untreated euploid mice showed no differences in total number of BrdU-positive cells (FIG. 11D), indicating that embryonic treatment with 7,8-DHF fully rescues the pool of neural precursor cells in the SVZ.

Effect of Treatment with 7,8-DHF on the Number of Proliferating Cells in the SGZ of Ts65Dn Mice Observation of FIG. 12A,B shows that in the SGZ of untreated Ts65Dn mice there were patently fewer BrdU-positive cells in comparison with euploid mice. Quantification of total cell number showed that while in the SGZ of Ts65Dn mice there were approximately 12850 BrdU-positive cells, in the SGZ of euploid mice there were approximately 17500 (FIG. 12D). These figures indicate that the number of proliferating cells in P2 Ts65Dn mice was −26% in comparison with euploid mice. Observation of FIG. 12B,C shows that embryonically-treated Ts65Dn mice had patently more BrdU-positive cells in comparison with their untreated counterparts. Quantification of total cell number showed that in the SGZ of treated Ts65Dn mice there were approximately 16800 BrdU-positive cells (FIG. 12D). These figures indicate that treated Ts65Dn mice underwent an increase in cell number of +30%. A comparison of treated Ts65Dn and untreated euploid mice showed no differences in total number of BrdU-positive cells (FIG. 12D), indicating that embryonic treatment with 7,8-DHF fully rescues the pool of neural precursor cells in the SGZ.

General effect of prenatal treatment with 7,8-DHF

The Ts65Dn strain is characterized by a high mortality rate during gestation (Roper et al., 2006). For this reason, the number of Ts65Dn pups in a litter results approximately 30% instead of the theoretical value of 50%. Moreover, Ts65Dn mice exhibit a high mortality rate before weaning (Roper et al., 2006). In view of the fragility of this strain, we deemed it important to establish whether treatment with 7,8-DHF has adverse effects on abortion rate, number of pups per litter, and viability and weight of P2 Ts65Dn (and euploid) mice.

We found that none of untreated and treated females underwent spontaneous abortion. No differences were found ($p=0.871$, two-tailed t test) in the mean number of pups per litter of vehicle-treated females (mean±ES: 5.60±0.84) and 7,8-DHF-treated females (mean±ES: 5.33±2.04). Likewise, no differences were found ($p=0.219$, two-tailed t test) in the mortality rate of the progeny of vehicle-treated females (mean±ES: 0.00±0.00) and 7,8-THF-treated females (mean±ES: 0.66±0.81).

The body and brain weight of P2 mice was evaluated in order to establish the effect of embryonic treatment on gross growth parameters. The LSD test confirmed well-established evidence that Ts65Dn mice have a reduced body weight in comparison with euploid mice (FIG. 13A) and showed that treatment did not further reduce the body weight of Ts65Dn mice. Consequently, treated Ts65Dn mice had a similar body weight as untreated Ts65Dn mice (FIG. 13A). In agreement with previous evidence (Guidi et al., 2014), untreated Ts65Dn mice had a smaller brain weight in comparison with euploid mice, although in the current experiments the difference did not reach statistical significance (FIG. 13B). Treated Ts65Dn mice had a reduced brain weight in comparison with euploid mice, but similar to that of untreated Ts65Dn mice (FIG. 13B), indicating that treatment has no adverse effect on the overall brain growth of Ts65Dn mice.

Prenatal Treatment with the BDNF Mimetic 7,8-DHF Restores Neurogenesis in the Forebrain Neurogenic Niches and has No Adverse Effects in Ts65Dn Mice Taken together these results suggest that treatment with 7,8-DHF has no adverse effects on the viability of the embryos and of the progeny. Although treatment does not improve the typically reduced body and brain weight of Ts65Dn mice, it does not further compromise the body and brain growth. These results show that prenatal treatment with 7,8-DHF has no adverse effects on the dams and on their progeny in terms of viability and growth. Thus, treatment with this natural compound appears to have a safe profile.

Treatment rescued the number of neural progenitor cells both in the SVZ and SGZ. These are the two major neurogenic niches of the forebrain. The SVZ is a neurogenic region that during embryonic development gradually replaces the VZ. The VZ and SVZ of the forebrain give origin to most of the neurons (and glia) that populate the forebrain. The SGZ is a neurogenic region that produces neurons (granule cells) and glia destined to the dentate gyrus. The observation that treatment positively impacts on both the SVZ and SGZ appears of relevance because it shows that treatment has an effect on the two major populations of neural progenitor cells of the forebrain.

A reduced number of neurons across the brain appears to underlie the disability in several cognitive domains that characterizes DS. Restoration of neurogenesis in the VZ/SVZ is a crucial prerequisite for restoration of cortical functions. Restoration of neurogenesis in the SGZ is a crucial prerequisite for restoration of hippocampus-dependent memory functions. Thus, the current findings suggest that prenatal treatment with 7,8-DHF may result in a generalized improvement of cognitive performance.

Conclusions

The finding that prenatal treatment with 7,8-DHF corrects neurogenesis in a model of DS opens a breakthrough for the rescue of cognitive impairment as it shows that it is possible to act "downstream" to triplicated genes, pharmacologically counteracting their negative effects.

SUPPLEMENTARY DATA

Supplementary data can be found in the article of Stagni et al. ("A flavonoid agonist of the TrkB receptor for BDNF improves hippocampal neurogenesis and hippocampus-dependent memory in the Ts65Dn mouse model of DS", Experimental Neurology 298, 2017, 79-96) incorporated by reference in its entirety.

REFERENCES

Alonso, M., Medina, J. H., Pozzo-Miller, L., 2004. ERK1/2 activation is necessary for BDNFto increase dendritic spine density in hippocampal CA1 pyramidal neurons. Learn. Mem. 11, 172-178.

Altman, J., Bayer, S., 1975. Postnatal development of the hippocampal dentate gyrus under normal and experimental conditions. In: Isaacson, R. L., Pribram, K. H. (Eds.), The Hippocampus, Vol 1. Plenum Press, New York and London (p 95-122. 95-122).

Altman, J., Bayer, S. A., 1990a. Migration and distribution of two populations of hippocampal granule cell precursors during the perinatal and postnatal periods. J. Comp. Neurol. 301, 365-381.

Altman, J., Bayer, S. A., 1990b. Mosaic organization of the hippocampal neuroepithelium and the multiple germinal sources of dentate granule cells. J. Comp. Neurol. 301, 325-342.

Arevalo, J. C., Wu, S. H., 2006. Neurotrophin signaling: many exciting surprises. Cell. Mol. Life Sci. 63, 1523-1537.

Bartesaghi, R., Guidi, S., Ciani, E., 2011. Is it possible to improve neurodevelopmental abnormalities in Down syndrome? Rev. Neurosci. 22, 419-455.

Belichenko, P. V., Kleschevnikov, A. M., Salehi, A., Epstein, C. J., Mobley, W. C., 2007. Synaptic and cognitive abnormalities in mouse models of Down syndrome: exploring genotype-phenotype relationships. J. Comp. Neurol. 504, 329-345.

Benavides-Piccione, R., Ballesteros-Yanez, I., de Lagran, M. M., Elston, G., Estivill, X., Fillat, C., Defelipe, J., Dierssen, M., 2004. On dendrites in Down syndrome and DS murine models: a spiny way to learn. Prog. Neurobiol. 74, 111-126.

Bianchi, P., Ciani, E., Contestabile, A., Guidi, S., Bartesaghi, R., 2010a. Lithium restores neurogenesis in the subventricular zone of the Ts65Dn mouse, a model for down syndrome. BrainPathol. 20, 106-118.

Bianchi, P., Ciani, E., Guidi, S., Trazzi, S., Felice, D., Grossi, G., Fernandez, M., Giuliani, A., Calza, L., Bartesaghi, R., 2010b. Early pharmacotherapy restores neurogenesis and cognitive performance in the Ts65Dn mouse model for Down syndrome. J. Neurosci. 30, 8769-8779.

Bibel, M., Hoppe, E., Barde, Y. A., 1999. Biochemical and functional interactions between the neurotrophin receptors trk and p75NTR. EMBO J. 18, 616-622.

Brazel C Y, Romanko M J, Rothstein R P, Levison S W (2003) Roles of the mammalian subventricular zone in brain development. Prog Neurobiol 69:49-69.

Busca, R., Pouyssegur, J., Lenormand, P., 2016. ERK1 and ERK2 map kinases: specific roles or functional redundancy? Front. Cell Dev. Biol. 4, 53.

Carlesimo, G. A., Marotta, L., Vicari, S., 1997. Long-term memory in mental retardation: evidence for a specific impairment in subjects with Down's syndrome. Neuropsychologia 35, 71-79.

Contestabile, A., Fila, T., Ceccarelli, C., Bonasoni, P., Bonapace, L., Santini, D., Bartesaghi, R., Ciani, E., 2007. Cell cycle alteration and decreased cell proliferation in the hippocampal dentate gyrus and in the neocortical germinal matrix of fetuses with Down syndrome and in Ts65Dn mice. Hippocampus 17, 665-678.

Contestabile, A., Greco, B., Ghezzi, D., Tucci, V., Benfenati, F., Gasparini, L., 2013. Lithium rescues synaptic plasticity and memory in Down syndrome mice. J. Clin. Invest. 123, 348-361.

Costa, A. C., Stasko, M. R., Schmidt, C., Davisson, M. T., 2010. Behavioral validation of the Ts65Dn mouse model for Down syndrome of a genetic background free of the retinal degeneration mutation Pde6b(rd1). Behav. BrainRes. 206, 52-62.

Delabar, J. M., Aflalo-Rattenbac, R., Creau, N., 2006. Developmental defects in trisomy 21 and mouse models. Scientific World Journal 6, 1945-1964.

Demas, G. E., Nelson, R. J., Krueger, B. K., Yarowsky, P. J., 1996. Spatial memory deficits in segmental trisomic Ts65Dn mice. Behav. Brain Res. 82, 85-92.

Dierssen, M., 2012. Down syndrome: the brain in trisomic mode. Nat. Rev. Neurosci. 13, 844-858.

Dorph Petersen, K. A., Nyengaard, J. R., Gundersen, H. J. G., 2001. Tissue shrinkage and unbiased stereological estimation of particle number and size. J. Microsc. 204, 232-246.

Foltran, R. B., Diaz, S. L., 2016. BDNF isoforms: a round trip ticket between neurogenesis and serotonin? J. Neurochem. 138, 204-221.

Gardiner, K. J., 2015. Pharmacological approaches to improving cognitive function in Down syndrome: current status and considerations. Drug Des. Devel. Ther. 9, 103-125.

Giacomini, A., Stagni, F., Trazzi, S., Guidi, S., Emili, M., Brigham, E., Ciani, E., Bartesaghi, R., 2015. Inhibition of APP gamma-secretase restores Sonic Hedgehog signaling and neurogenesis in the Ts65Dn mouse model of Down syndrome. Neurobiol. Dis. 82, 385-396.

Haniu, M., Montestruque, S., Bures, E. J., Talvenheimo, J., Toso, R., Lewis-Sandy, S., Welcher, A. A., Rohde, M. F., 1997. Interactions between brain-derived neurotrophic factor and the TRKB receptor. Identification of two ligand binding domains in soluble TRKB by affinity separation and chemical cross-linking. J. Biol. Chem. 272, 25296-25303.

Haydar, T. F., Reeves, R. H., 2012. Trisomy 21 and early brain development. Trends Neurosci. 35, 81-91.

Iivonen, H., Nurminen, L., Harri, M., Tanila, H., Puolivali, J., 2003. Hypothermia in mice tested in Morris water maze. Behav. Brain Res. 141, 207-213.

Kempermann, G., Gage, F. H., 2002. Genetic influence on phenotypic differentiation inadult hippocampal neurogenesis. Brain Res. Dev. Brain Res. 134, 1-12.

Lefloch, R., Pouyssegur, J., Lenormand, P., 2008. Single and combined silencing of ERK1 and ERK2 reveals their positive contribution to growth signaling depending on their expressionlevels. Mol. Cell. Biol. 28, 511-527.

Liu, X., Chan, C.-B., Jang, S.-W., Pradoldej, S., Huang, J., He, K., Phun, L. H., France, S., Xiao, G., Jia, Y., Luo, H. R., Ye, K., 2010. A synthetic 7,8-dihydroxyflavone derivative promotes neurogenesis and exhibits potent antidepressant effect. J. Med. Chem. 53, 8274-8286.

Liu, X., Qi, Q., Xiao, G., Li, J., Luo, H. R., Ye, K., 2013. O-methylated metabolite of 7,8-dihydroxyflavone activates TrkB receptor and displays antidepressant activity. Pharmacology 91, 185-200.

Liu, C., Chan, C. B., Ye, K., 2016. 7,8-Dihydroxyflavone, a small molecular TrkB agonist, is useful for treating various BDNF-implicated human disorders. Transl. Neurodegener. 5,2.

Malberg, J. E., Eisch, A. J., Nestler, E. J., Duman, R. S., 2000. Chronic antidepressant treatment increases neurogenesis in adult rat hippocampus. J. Neurosci. 20, 9104-9110.

Meneghini, V., Cuccurazzu, B., Bortolotto, V., Ramazzotti, V., Ubezio, F., Tzschentke, T. M., Canonico, P. L., Grilli, M., 2014. The noradrenergic component in tapentadol action counteracts mu-opioid receptor-mediated adverse effects on adult neurogenesis. Mol. Pharmacol. 85, 658-670.

Nowakowski, R. S., Lewin, S. B., Miller, M. W., 1989. Bromodeoxyuridine im munohistochemical determination of the lengths of the cell cycle and the DNA-synthetic phase for an anatomically defined population. J. Neurocytol. 18, 311-318.

Paxinos G, Halliday G, Watson C, Koutcherov Y, Wang H (2007) Atlas of the developing mouse brain, Academic Press, Elsevier, pp 356. 2007.

Reefhuis, J., Devine, O., Friedman, J. M., Louik, K., Honein, M., 2015. Specific SSRIs and birth defects: Bayesian analysis to interpret new data in the context of previous re-ports. BMJ350, h3190.

Reinholdt, L. G., Ding, Y., Gilbert, G. J., Czechanski, A., Solzak, J. P., Roper, R. J., Johnson, M. T., Donahue, L. R., Lutz, C., Davisson, M. T., 2011. Molecular characterization of the translocation breakpoints in the Down syndrome mouse model Ts65Dn. Mamm. Genome 22, 685-691.

Rendeiro, C., Rhodes, J. S., Spencer, J. P. E., 2015. The mechanisms of action of flavonoids in the brain: direct versus indirect effects. Neurochem. Int. 89, 126-139.

Rice, D., Barone, S., 2010. Critical periods of vulnerabiliy for the developing nervpus system: evidence from humans and animal models. Environ. Health Perspect. 108 (Suppl. 3), 511-533.

Rolls, E. T., 2016. Pattern separation, completion, and categorisation in the hippocampus and neocortex. Neurobiol. Learn. Mem. 129, 4-28.

Roper, R. J., St John, H. K., Philip, J., Lawler, A., Reeves, R. H., 2006. Perinatal loss of Ts65Dn Down syndrome mice. Genetics 172, 437-443.

Rose, C. R., Blum, R., Pichler, B., Lepier, A., Kafitz, K. W., Konnerth, A., 2003. Truncated TrkB-T1 mediates neurotrophin-evoked calcium signalling in glia cells. Nature 426, 74-78.

Salehi, A., Faizi, M., Colas, D., Valletta, J., Laguna, J., Takimoto-Kimura, R., Kleschevnikov, A., Wagner, S. L., Aisen, P., Shamloo, M., Mobley, W. C., 2009. Restoration of norepinephrine-modulated contextual memory in a mouse model of Down syndrome. Sci. Transl. Med (1:7ra17).

Seress, L., Abraham, H., Tornoczky, T., Kosztolanyi, G., 2001. Cell formation in the human hippocampal formation from mid-gestation to the late postnatal period. Neuroscience 105, 831-843.

Spalding, K. L., Bergmann, O., Alkass, K., Bernard, S., Salehpour, M., Huttner, H. B., Bostrom, E., Westerlund, I., Vial, C., Buchholz, B. A., Possnert, G., Mash, D. C., Druid, H., Frisen, J., 2013.

Dynamics of hippocampal neurogenesis in adult humans. Cell 153, 1219-1227.

Spencer, J. P., 2008. Flavonoids: modulators of brain function? Br. J. Nutr. 99 (E Suppl 1), ES60-77.

Stagni F, Giacomini A, Guidi S, Emili M, Uguagliati B, Salvalai M E, Bortolotto V, Grilli M, Rimondini R, Bartesaghi R (2017) A flavonoid agonist of the TrkB receptor for BDNF improves hippocampal neurogenesis and hippocampus-dependent memory in the Ts65Dn mouse model of DS. Exp Neurol 298:79-96.

Stiles, J., Jernigan, T. L., 2010. The basics of brain development. Neuropsychol. Rev. 20, 327-348.

Toiber, D., Azkona, G., Ben-Ari, S., Toran, N., Soreq, H., Dierssen, M., 2010. Engineering DYRKIA overdosage yields Down syndrome-characteristic cortical splicing aberra-tions. Neurobiol. Dis. 40, 348-359.

Tozuka, Y., Fukuda, S., Namba, T., Seki, T., Hisatsune, T., 2005. GABAergic excitation promotes neuronal differentiation in adult hippocampal progenitor cells. Neuron 47, 803-815.

Trazzi, S., Mitrugno, V. M., Valli, E., Fuchs, C., Rizzi, S., Guidi, S., Perini, G., Bartesaghi, R., Ciani, E., 2011. APP-dependent up-regulation of Ptch1 underlies proliferation impairment of neural precursors in Down syndrome. Hum. Mol. Genet. 20, 1560-1573.

Trazzi, S., Fuchs, C., Valli, E., Perini, G., Bartesaghi, R., Ciani, E., 2013. The amyloid precursor protein (APP) triplicated gene impairs neuronal precursor differentiation and neurite development through two different domains in the Ts65Dn mouse model for Down syndrome. J. Biol. Chem. 288, 20817-20829.

Trazzi, S., Fuchs, C., De Franceschi, M., Mitrugno, V., Bartesaghi, R., Ciani, E., 2014. APP-dependent alteration of GSK3β activity impairs neurogenesis in the Ts65Dn mouse model of Down syndrome. Neurobiol. Dis. 64, 27-36.

Tsai, T., Klausmeyer, A., Conrad, R., Gottschling, C., Leo, M., Faissner, A., Wiese, S., 2013. 7,8-Dihydroxyflavone leads to survival of cultured embryonic motoneurons by acti-vating intracellular signaling pathways. Mol. Cell. Neurosci. 56, 18-28.

Vicari, S., Bellucci, S., Carlesimo, G. A., 2000. Implicit and explicit memory: a functional dissociationin persons with Down syndrome. Neuropsychologia 38, 240-251.

Vilar, M., Mira, H., 2016. Regulation of neurogenesis by neurotrophins during adulthood: expected and unexpected roles. Front. Neurosci. 10,26.

Vorhees, C. V., Williams, M. T., 2006. Morris water maze: procedures for assessing spatial and related forms of learning and memory. Nat. Protoc. 1, 848-858.

Williams, R. J., Spencer, J. P., 2012. Flavonoids, cognition, and dementia: actions, me chanisms, and potential therapeutic utility for Alzheimer disease. Free Radic. Biol. Med. 52, 35-45.

Workman, A. D., Charvet, C. J., Clancy, B., Darlington, R. B., Finlay, B. L., 2013. Modeling transformations of neurodevelopmental sequences across mammalian species. J. Neurosci. 33, 7368-7383.

Zeng, Y., Liu, Y., Wu, M., Liu, J., Hu, Q., 2012. Activation of TrkB by 7,8-dihydroxy-flavone prevents fear memory defects and facilitates amygdalar synaptic plasticity in aging. J. Alzheimers Dis. 31, 765-778.

TABLE 1

Antibodies used for immunohistochemistry and Western blotting.

| Antigen | Application | Antibody dilution-manufactures |
|---|---|---|
| α-Tubulin | WB | Primary: mouse monoclonal 1:1000 (Clone B-5-1-2) (Sigma-Aldrich, T5168) <br> Secondary: HRP-conjugated anti-mouse 1:20000 (Jackson Immunoresearch, 115-035-003) |
| Brain-derived neurotrophic factor (BDNF) | WB | Primary: rabbit polyclonal 1:500 (N-20) (Santa Cruz Biotechnology, cs-546) <br> Secondary: HRP-conjugated anti-rabbit: 1:10000 (Jackson Immunoresearch, 111-035-003) |
| 5-Bromo-2-deoxyuridine (BrdU) | IHC | Primary: rat monoclonal 1:200 (BioRad, OBT0030) <br> Secondary: Cy3-conjugated anti-rat IgG 1:200 (Jackson Immunoresearch, 112-165-143) |
| Extracellular signal-regulated kinase (ERK1/2) | WB | Primary: mouse monoclonal 1:1000 (3A7) (Cell Signaling Technology, 9107) <br> Secondary: HRP-conjugated anti-mouse 1:10000 (Jackson Immunoresearch, 115-035-003) |
| phosphorylated ERK (p-ERK1/2) | WB | Primary: rabbit polyclonal 1:1000 (Cell Signaling Technology, 9101) <br> Secondary: HRP-conjugated anti-rabbit: 1:10000 (Jackson Immunoresearch, 111-035-003) |
| Glyceraldehyde 3-phosphate dehydrogenase (GAPDH) | WB | Primary: rabbit polyclonal 1:5000 (Sigma-Aldrich, G9545) <br> Secondary: HRP-conjugated anti-rabbit: 1:10000 (Jackson Immunoresearch, 111-035-003) |
| Synaptophysin (SYN) | WB | Primary: rabbit polyclonal 1:1000 (Abcam, ab 14692) <br> Secondary: HRP-conjugated anti-rabbit: 1:10000 (Jackson Immunoresearch, 111-035-003) |

TABLE 1-continued

Antibodies used for immunohistochemistry and Western blotting.

| Antigen | Application | Antibody dilution-manufactures |
|---|---|---|
| Tropomyosin receptor kinase (Trk) B Full Length (FL) and TrkB truncated (T1) | WB | Primary: rabbit monoclonal 1:1000 (Cell Signaling Technology, 80E3) Secondary: HRP-conjugated anti-rabbit: 1:10000 (Jackson Immunoresearch, 111-035-003) |
| Phosphorylated TrkB-FL (p-TrkB-FL) | WB | Primary: rabbit polyclonal 1:1000 (Millipore, ABN1381) Secondary: HRP-conjugated anti-rabbit: 1:10000 (Jackson Immunoresearch, 111-035-003) |

Abbreviations:

IHC, immunohistochemistry;

WB, Western blotting.

TABLE 2

Learning phase of the Morris Water Maze: p values of the Fisher LSD test for the indicated variables

| | | Latency | | | | | Time periphery (sec) | | |
|---|---|---|---|---|---|---|---|---|---|
| | | D1 | D2 | D3 | D4 | D5 | D1 | D2 | D3 |
| Eu + Veh | Ts + Veh | 0.054 | 0.041 | 0.001 | 0.006 | <0.001 | 0.081 | 0.140 | 0.028 |
| | Eu + 7,8-DHF | 0.415 | 0.013 | 0.083 | 0.068 | 0.171 | 0.837 | 0.002 | 0.041 |
| | Ts + 7,8-DHF | 0.127 | 0.162 | 0.045 | 0.078 | 0.412 | 0.131 | 0.215 | 0.532 |
| Ts + Veh | Eu + 7,8-DHF | 0.246 | <0.001 | <0.001 | <0.001 | <0.001 | 0.120 | <0.001 | <0.001 |
| | Ts + 7,8-DHF | 0.665 | 0.491 | 0.181 | 0.284 | 0.002 | 0.787 | 0.796 | 0.111 |
| Eu + 7,8-DHF | Ts + 7,8-DHF | 0.461 | <0.001 | <0.001 | 0.001 | 0.033 | 0.190 | <0.001 | 0.009 |

| | | Time periphery (sec) | | Time periphery (%) | | | | |
|---|---|---|---|---|---|---|---|---|
| | | D4 | D5 | D1 | D2 | D3 | D4 | D5 |
| Eu + Veh | Ts + Veh | 0.011 | 0.001 | 0.258 | 0.472 | 0.242 | 0.123 | 0.094 |
| | Eu + 7,8-DHF | 0.152 | 0.177 | 0.784 | <0.001 | 0.007 | 0.013 | 0.009 |
| | Ts + 7,8-DHF | 0.273 | 0.939 | 0.152 | 0.189 | 0.799 | 0.983 | 0.634 |
| Ts + Veh | Eu + 7,8-DHF | <0.001 | <0.001 | 0.384 | <0.001 | <0.001 | <0.001 | <0.001 |
| | Ts + 7,8-DHF | 0.133 | 0.001 | 0.783 | 0.569 | 0.363 | 0.124 | 0.036 |
| Eu + 7,8-DHF | Ts + 7,8-DHF | 0.014 | 0.210 | 0.243 | <0.001 | 0.004 | 0.016 | 0.034 |

| | | Path length | | | | | Proximity | | |
|---|---|---|---|---|---|---|---|---|---|
| | | D1 | D2 | D3 | D4 | D5 | D1 | D2 | D3 |
| Eu + Veh | Ts + Veh | 0.022 | 0.473 | 0.129 | 0.449 | 0.028 | 0.382 | 0.620 | 0.323 |
| | Eu + 7,8-DHF | 0.269 | 0.103 | 0.905 | 0.111 | 0.660 | 0.180 | 0.003 | 0.006 |
| | Ts + 7,8-DHF | 0.020 | 0.342 | 0.413 | 0.712 | 0.685 | 0.293 | 0.719 | 0.877 |
| Ts + Veh | Eu + 7,8-DHF | 0.208 | 0.383 | 0.103 | 0.024 | 0.010 | 0.669 | 0.014 | <0.001 |
| | Ts + 7,8-DHF | 0.996 | 0.830 | 0.475 | 0.697 | 0.011 | 0.874 | 0.404 | 0.411 |
| Eu + 7,8-DHF | Ts + 7,8-DHF | 0.198 | 0.504 | 0.350 | 0.054 | 0.978 | 0.786 | 0.001 | 0.005 |

| | | Proximity | | Swim speed | | | | |
|---|---|---|---|---|---|---|---|---|
| | | D4 | D5 | D1 | D2 | D3 | D4 | D5 |
| Eu + Veh | Ts + Veh | 0.050 | 0.012 | 0.055 | 0.297 | 0.474 | 0.402 | 0.140 |
| | Eu + 7,8-DHF | 0.037 | 0.017 | 0.010 | 0.514 | 0.776 | 0.344 | 0.705 |
| | Ts + 7,8-DHF | 0.557 | 0.245 | 0.003 | 0.003 | 0.006 | 0.056 | 0.051 |
| Ts + Veh | Eu + 7,8-DHF | <0.001 | <0.001 | 0.550 | 0.677 | 0.328 | 0.939 | 0.263 |
| | Ts + 7,8-DHF | 0.162 | 0.001 | 0.299 | 0.048 | 0.042 | 0.296 | 0.652 |
| Eu + 7,8-DHF | Ts + 7,8-DHF | 0.009 | 0.215 | 0.639 | 0.015 | 0.003 | 0.315 | 0.111 |

The numbers in bold correspond to statistically significant differences.

Abbreviations: 7,8-DHF, 7,8-dihydroxyflavone; D, day; Eu, euploid; sec, seconds; Ts, Ts65Dn; Veh, vehicle.

TABLE 3

Number of mice included and excluded from the analyses.

|  | Euploid + Vehicle | | | Ts65Dn + Vehicle | | |
| --- | --- | --- | --- | --- | --- | --- |
|  | N. of mice entered in the experiment | N. of mice excluded from the analysis | N. of mice used for statistical analysis | N. of mice entered in the experiment | N. of mice excluded from the analysis | N. of mice used for statistical analysis |
| Brain Weight P15 | 35 | — | 35 | 21 | — | 21 |
| Body Weight P15 | 35 | — | 35 | 21 | — | 21 |
| Brain Weight P45 | 19 | — | 19 | 14 | — | 14 |
| Body Weight P45 | 19 | — | 19 | 14 | — | 14 |
| BrdU + Cells (DG) | 7 | — | 7 | 8 | — | 8 |
| N. of granule cells (DG) | 4 | — | 4 | 4 | — | 4 |
| Spine density (ML) | 4 | — | 4 | 4 | — | 4 |
| SYN (Hippocampus) | 10 | — | 10 | 10 | — | 10 |
| BDNF (Hippocampus) | 21 | 1 | 20 | 21 | — | 21 |
| TrkB-FL (Hippocampus) | 21 | 2 | 19 | 21 | 2 | 19 |
| p-TrkB (Hippocampus) | 17 | 2 | 15 | 17 | 1 | 16 |
| TrkB-T1 (Hippocampus) | 21 | 2 | 19 | 21 | — | 21 |
| p-ERK1(Hippocampus) | 12 | 2 | 10 | 13 | 1 | 12 |
| ERK1 tot (Hippocampus) | 12 | 2 | 10 | 13 | 2 | 11 |
| p-ERK2 (Hippocampus) | 12 | 2 | 10 | 13 | 1 | 12 |
| ERK2 tot (Hippocampus) | 12 | 1 | 11 | 13 | 1 | 12 |
| MWM (Learning + Probe) | 19 | 3 | 16 | 14 | — | 14 |

|  | Euploid + 7,8-DHF | | | Ts65Dn + 7,8-DHF | | |
| --- | --- | --- | --- | --- | --- | --- |
|  | N. of mice entered in the experiment | N. of mice excluded from the analysis | N. of mice used for statistical analysis | N. of mice entered in the experiment | N. of mice excluded from the analysis | N. of mice used for statistical analysis |
| Brain Weight P15 | 25 | — | 25 | 15 | — | 15 |
| Body Weight P15 | 25 | — | 25 | 15 | — | 15 |
| Brain Weight P45 | 17 | — | 17 | 16 | — | 16 |
| Body Weight P45 | 17 | — | 17 | 16 | — | 16 |
| BrdU + Cells (DG) | 3 | — | 3 | 5 | — | 5 |
| N. of granule cells (DG) | 4 | — | 4 | 5 | — | 5 |
| Spine density (ML) | 4 | — | 4 | 4 | — | 4 |
| SYN (Hippocampus) | 5 | — | 5 | 6 | — | 6 |
| BDNF (Hippocampus) | 5 | — | 5 | 6 | — | 6 |
| TrkB-FL (Hippocampus) | 5 | — | 5 | 6 | — | 6 |
| p-TrkB (Hippocampus) | 5 | — | 5 | 6 | — | 6 |
| TrkB-T1 (Hippocampus) | 5 | — | 5 | 6 | — | 6 |
| p-ERK1(Hippocampus) | 5 | — | 5 | 6 | — | 6 |
| ERK1 tot (Hippocampus) | 5 | — | 5 | 6 | — | 6 |
| p-ERK2 (Hippocampus) | 5 | — | 5 | 6 | — | 6 |
| ERK2 tot (Hippocampus) | 5 | — | 5 | 6 | — | 6 |
| MWM (Learning + Probe) | 17 | 1 | 16 | 16 | 1 | 15 |

Abbreviations: 7,8-DHF, 7,8-dihydroxyflavone; DG, dentate gyrus; ML, molecular layer of the dentate gyrus; N., number; P, post-natal day.

TABLE 4

P values of Fisher LSD test for the indicated variables.

|  |  | Cultures of NPCs | | | | |
| --- | --- | --- | --- | --- | --- | --- |
|  |  | SVZ Proliferation | SVZ MaP2+/Nestin− Cells | SVZ MaP2−/Nestin+ Cells | SGZ % Differenziated Cells | SVZ % Differenziated Cells |
| Ts + standard | Ts + 0.3 µM 7,8-DHF | .170 | .006 | .063 | .259 | .515 |
|  | Ts + 1 µM 7,8-DHF | .459 | <.001 | .957 | .077 | .012 |
|  | Ts + 3 µM 7,8-DHF | .397 | <.001 | .606 | .056 | .006 |
|  | Ts + 5 µM 7,8-DHF | .221 | <.001 | .281 | .005 | <.001 |
|  | Ts + 10 µM 7,8-DHF | <.001 | .003 | .985 | .002 | .001 |
| Ts + 0.3 µM 7,8-DHF | Ts + 1 µM 7,8-DHF | .046 | .081 | .069 | .467 | .004 |
|  | Ts + 3 µM 7,8-DHF | .037 | .135 | .154 | .373 | .002 |
|  | Ts + 5 µM 7,8-DHF | .018 | .018 | .375 | .041 | <.001 |
|  | Ts + 10 µM 7,8-DHF | <.001 | .719 | .065 | .015 | <.001 |
| Ts + 1 µM 7,8-DHF | Ts + 3 µM 7,8-DHF | .910 | .767 | .643 | .865 | .689 |
|  | Ts + 5 µM 7,8-DHF | .608 | .423 | .303 | .149 | .022 |
|  | Ts + 10 µM 7,8-DHF | <.001 | .150 | .972 | .060 | .135 |

TABLE 4-continued

P values of Fisher LSD test for the indicated variables.

| | | Cultures of NPCs | | | | |
|---|---|---|---|---|---|---|
| | | SVZ Proliferation | SVZ MaP2+/Nestin− Cells | SVZ MaP2−/Nestin+ Cells | SGZ % Differenziated Cells | SVZ % Differenziated Cells |
| Ts + 3 μM 7,8-DHF | Ts + 5 μM 7,8-DHF | .687 | .280 | .560 | .046 | .196 |
| | Ts + 10 μM 7,8-DHF | <.001 | .240 | .619 | .256 | .081 |
| Ts + 5 μM 7,8-DHF | Ts + 10 μM 7,8-DHF | .000 | .035 | .288 | .320 | .603 |

The numbers in bold correspond to statistically significant differences.
Abbreviations: 7,8-DHF, 7,8-dihydroxyflavone; NPCs, neural progenitor cells; SGZ, subgranular zone of the dentate gyrus; SVZ, subventricular zone; Ts, Ts65Dn.

TABLE 5

P values of Fisher LSD test for the indicated variables.

| | | P15 | | P45 | |
|---|---|---|---|---|---|
| | | Body Weight | Brain Weight | Body Weight | Brain Weight |
| Eu + Veh | Ts + Veh | .001 | .004 | .017 | .029 |
| | Eu + 7,8-DHF | .159 | .005 | .032 | .291 |
| | Ts + 7,8-DHF | .001 | <.001 | .006 | .206 |
| Ts + Veh | Eu + 7,8-DHF | .039 | .832 | .715 | .234 |
| | Ts + 7,8-DHF | .921 | .363 | .764 | .335 |
| Eu + 7,8-DHF | Ts + 7,8-DHF | .049 | .258 | .489 | .823 |

The numbers in bold correspond to statistically significant differences.
Abbreviations:
7,8-DHF, 7,8-dihydroxyflavone;
Eu, euploid;
P, postnatal day;
Ts, Ts65Dn;
Veh, Vehicle.

TABLE 6

P values of Fisher LSD test for the indicated variables.

| | | P15 | | |
|---|---|---|---|---|
| | | BrdU + Cells DG | N. of Granule Cells DG | Spine Density DG |
| Eu + Veh | Ts + Veh | <.001 | .013 | <.001 |
| | Eu + 7,8-DHF | .344 | .248 | .066 |
| | Ts + 7,8-DHF | .025 | .584 | .175 |
| Ts + Veh | Eu + 7,8-DHF | .001 | .116 | <.001 |
| | Ts + 7,8-DHF | .003 | .027 | <.001 |
| Eu + 7,8-DHF | Ts + 7,8-DHF | .314 | .488 | .570 |

The numbers in bold correspond to statistically significant differences.
Abbreviations:
7,8-DHF, 7,8-dihydroxyflavone;
DG, dentate gyrus;
Eu, euploid;
N., number;
P, postnatal day;
Ts, Ts65Dn;
Veh, Vehicle.

TABLE 7

P values of Fisher LSD test for the indicated variables.

| | | P15 | | | | | | | | |
|---|---|---|---|---|---|---|---|---|---|---|
| | | SYN Hippo | BDNF Hippo | TrkB-FL Hippo | pTrkB-FL/ TrkB-FL Hippo | TrkB-T1 Hippo | pERK1/ ERK1 tot Hippo | ERK1 tot Hippo | pERK2/ ERK2 tot Hippo | ERK2 tot Hippo |
| Eu + Veh | Ts + Veh | .059 | .746 | .336 | .149 | .278 | .108 | .269 | .139 | .958 |
| | Eu + 7,8-DHF | .262 | .172 | .894 | .024 | .668 | .409 | .479 | .354 | .031 |
| | Ts + 7,8-DHF | .357 | .012 | .005 | .002 | .021 | .001 | .220 | .027 | .006 |
| Ts + Veh | Eu + 7,8-DHF | .013 | .117 | .624 | .180 | .794 | .726 | .134 | .043 | .026 |
| | Ts + 7,8-DHF | .017 | .006 | .026 | .026 | .003 | .027 | .036 | .272 | .005 |
| Eu + 7,8-DHF | Ts + 7,8-DHF | .815 | .386 | .034 | .511 | .033 | .042 | .739 | .010 | .791 |

The numbers in bold correspond to statistically significant differences.
Abbreviations: 7,8-DHF, 7,8-dihydroxyflavone; Eu, euploid; Hippo, hippocampus; P, postnatal day; Ts, Ts65Dn; Veh, Vehicle.

TABLE 8

P values of Fisher LSD test for the indicated variables.

|  |  | Morris Water Maze Probe test | | | | |
|---|---|---|---|---|---|---|
|  |  | Latency | Frequency | Proximity | Time Periphery (%) | Swimspeed |
| Eu + Veh | Ts + Veh | .005 | .031 | .019 | .923 | .998 |
|  | Eu + 7,8-DHF | .382 | .052 | .318 | .003 | .344 |
|  | Ts + 7,8-DHF | .454 | .754 | .743 | .049 | .993 |
| Ts + Veh | Eu + 7,8-DHF | <.001 | <.001 | .001 | .006 | .359 |
|  | Ts + 7,8-DHF | .038 | .066 | .009 | .069 | .347 |
| Eu + 7,8-DHF | Ts + 7,8-DHF | .111 | .027 | .511 | .312 | .589 |

The numbers in bold correspond to statistically significant differences.
Abbreviations: 7,8-DHF, 7,8-dihydroxyflavone; Eu, euploid; Ts, Ts65Dn; Veh, Vehicle.

TABLE 9

P values of two-sample paired t-test test for the indicated variable.

|  |  | Morris Water Maze Probe test % time spent in quadrant |
|---|---|---|
| Eu + Veh platform quadrant | Eu + Veh NW quadrant | .150 |
|  | Eu + Veh NE quadrant | .008 |
|  | Eu + Veh SE quadrant | .047 |
| Ts + Veh platform quadrant | Ts + Veh NW quadrant | .394 |
|  | Ts + Veh NE quadrant | .426 |
|  | Ts + Veh SE quadrant | .909 |
| Eu + 7,8-DHF platform quadrant | Eu + 7,8-DHF NW quadrant | .801 |
|  | Eu + 7,8-DHF NE quadrant | .002 |
|  | Eu + 7,8-DHF SE quadrant | <.001 |
| Ts + 7,8-DHF platform quadrant | Ts + 7,8-DHF NW quadrant | .101 |
|  | Ts + 7,8-DHF NE quadrant | .029 |
|  | Ts + 7,8-DHF SE quadrant | .059 |

The numbers in bold correspond to statistically significant differences.
Abbreviations:
7,8-DHF, 7,8-dihydroxyflavone;
Eu, euploid;
NE, north-east;
NW, north-west;
SE, south-east;
Ts, Ts65Dn;
Veh, Vehicle.

TABLE 10

Effect of treatment with 7,8-DHF on ERK1/2 stoichiometry.

|  | Eu + Veh | | Ts65Dn + Veh | | Eu + 7,8-DHF | | Ts65Dn + 7,8-DHF | |
|---|---|---|---|---|---|---|---|---|
|  | Mean | SE | Mean | SE | Mean | SE | Mean | SE |
| ERK2/ERK1 | 3.36 | 0.25 | 3.40 | 0.18 | 4.18 | 0.35 | 3.93 | 0.315 |
| p-ERK2/p-ERK1 | 2.19 | 0.09 | 2.11 | 0.08 | 2.32 | 0.48 | 2.01 | 0.10 |

Values represent the ratio between ERK2 and ERK1 and between p-ERK2 and p-ERK1 in the hippocampal region of euploid (Eu) and Ts65Dn mice that received either vehicle (Veh) or 7,8-DHF in the period P3-P15. Same mice as in FIG. 6F, G. A post hoc Fisher LSD test after two-way ANOVA showed no difference among groups.

We claim:

1. A method of decreasing likelihood of developing intellectual disability in subjects affected by Down syndrome said method comprising:

administering a pharmaceutical composition comprising an effective amount of a TrkB receptor agonist to said subjects and decreasing the likelihood of said intellectual disability in said subjects, wherein said TrkB receptor agonist is 7,8-dihydroxyflavone.

2. The method of claim 1, wherein said administering step takes places prenatally.

3. The method of claim 1, wherein said administering step takes places perinatally.

4. The method of claim 1, wherein said administering step takes places neonatally.

5. A method of treating intellectual disability in subjects affected by Down syndrome said method comprising:

administering a pharmaceutical composition comprising an effective amount of a TrkB receptor agonist to said subjects and treating said intellectual disability in said subjects, wherein said TrkB receptor agonist is 7,8-dihydroxyflavone.

6. The method of claim 5, wherein said administering step takes places prenatally.

7. The method of claim 5, wherein said administering step takes places perinatally.

8. The method of claim 5, wherein said administering step takes places neonatally.

* * * * *